US008642357B2

(12) United States Patent
Elias et al.

(10) Patent No.: US 8,642,357 B2
(45) Date of Patent: Feb. 4, 2014

(54) SEMAPHORIN 7A PLAYS A CRITICAL ROLE IN TGF-$\beta_1$-INDUCED PULMONARY FIBROSIS AND ALVEOLAR DESTRUCTION

(75) Inventors: Jack A. Elias, Woodbridge, CT (US); Chun Geun Lee, New Haven, CT (US)

(73) Assignee: Yale University, New Haven, CT (US)

( * ) Notice: Subject to any disclaimer, the term of this patent is extended or adjusted under 35 U.S.C. 154(b) by 393 days.

(21) Appl. No.: 12/604,192

(22) Filed: Oct. 22, 2009

(65) Prior Publication Data
US 2010/0104570 A1 Apr. 29, 2010

(51) Int. Cl.
*G01N 33/53* (2006.01)
*A61K 39/395* (2006.01)
*C12Q 1/68* (2006.01)
*C12N 15/11* (2006.01)
*C12N 15/113* (2010.01)
*A61K 38/00* (2006.01)

(52) U.S. Cl.
USPC ........... 436/547; 436/543; 436/544; 436/545; 436/546; 436/548; 424/130.1; 424/141.1; 424/142.1; 424/135.1; 424/178.1; 514/44 A; 514/1.8

(58) Field of Classification Search
None
See application file for complete search history.

(56) References Cited

U.S. PATENT DOCUMENTS 7,462,461 B2 12/2008 Kikutani

OTHER PUBLICATIONS

Wynn. J. Pathol. 2008; 214: 199-210.*
Burgess et al. J of Cell Bio. 1990, 111:2129-2138.*
Bowie et al. Science, 1990, 247:1306-1310.*
Pawson et al. 2003, Science 300:445-452.*
Rudikoff et al. Proc. Natl. Acad. Sci. USA 1982 vol. 79: p. 1979.*
Bergeron et al., "*Cytokine profiles in idiopathic pulmonary fibrosis suggest an important role for TGF-beta and IL-10.*" 2003, Eur Respir J. 22:69-76.
Boxall et al., "*The contribution of transforming growth factor-beta and epidermal growth factor signalling to airway remodelling in chronic asthma.*" 2006, Eur Respir J. 27:208-229.
Czopik et al., "*Semaphorin 7A is a negative regulator of T cell responses.*" 2006, Immunity 24:591-600.
Daniels et al., "*Imatinib mesylate inhibits the profibrogenic activity of TGF-beta and prevents bleomycin-mediated lung fibrosis.*" 2004, J Clin Invest. 114:1308-1316.
Delorme et al., "*Expression and function of semaphorin 7A in bone cells.*" 2005, Biol Cell 97:589-597.
Elias et al., "*Airway remodeling in asthma.*" 1999, J Clin Invest. 104:1001-1006.
Elias et al., "*New insights into the pathogenesis of asthma.*" 2003, J Clin Invest. 111:291-297.
Howell et al., "*TGF-beta: its role in asthma and therapeutic potential.*" 2006, Curr Drug Targets 7:547-565.
Kang et al., "*Semaphorin 7A plays a critical role in TGF-beta1-induced pulmonary fibrosis.*" 2007, J. Exp. Med, 204:1083-93.
Khalil et al., "*TGF-beta 1, but not TGF-beta 2 or TGF-beta 3, is differentially present in epithelial cells of advanced pulmonary fibrosis: an immunohistochemical study.*" 1996, Am J Respir Cell Mol Biol. 14:131-138.
Khalil et al., "*Regulation of the effects of TGF-beta 1 by activation of latent TGF-beta 1 and differential expression of TGF-beta receptors (T beta R-I and T beta R-II) in idiopathic pulmonary fibrosis.*" 2001, Thorax 56:907-915.
Krein et al., "*Roles for insulin-like growth factor I and transforming growth factor-beta in fibrotic lung disease.*" 2002 Chest 122:289S-293S.
Leask et al., "*TGF-beta signaling and the fibrotic response.*" 2004, FASEB J. 18:816-827.
Lee et al., "*Early growth response gene 1-mediated apoptosis is essential for transforming growth factor beta1-induced pulmonary fibrosis.*" 2004, J Exp Med. 200:377-389.
Martin et al., "*TGF-beta1 and radiation fibrosis: a master switch and a specific therapeutic target?*" 2000, Int J Radiat Oncol Biol Phys. 47:277-290.
Nakao et al., "*Transient gene transfer and expression of Smad7 prevents bleomycin-induced lung fibrosis in mice.*" 1999, J Clin Invest. 104:5-11.
Nakatani-Okuda et al., "*Protection against bleomycin-induced lung injury by IL-18 in mice.*" 2005, Am J Physiol Lung Cell Mol Physiol. 289:L280-287.
Pasterkamp et al., "*Semaphorin 7A promotes axon outgrowth through integrins and MAPKs.*" 2003, Nature 424:398-405.
Pendergast, "*The Abl family kinases: mechanisms of regulation and signaling.*" 2002, Adv Cancer Res. 85:51-100.
Steen, "*Targeted therapy for systemic sclerosis.*" 2006, Autoimmun Rev. 5:122-124.
Suzuki et al., "*Semaphorin 7A initiates T-cell-mediated inflammatory responses through alpha1beta1 integrin.*" 2007 Nature 446:680-4.
Xu et al., "*Release of biologically active TGF-beta1 by alveolar epithelial cells results in pulmonary fibrosis.*" 2003, Am J. Physiol Lung Cell Mol Physiol. 285:L527-539.
Yehualaeshet et al., "*A CD36 synthetic peptide inhibits bleomycin-induced pulmonary inflammation and connective tissue synthesis in the rat.*" 2000, Am J Respir Cell Mol Biol. 23:204-212.
Zheng et al., "*Inducible targeting of IL-13 to the adult lung causes matrix metalloproteinase-and cathepsin-dependent emphysema.*" 2000, J Clin Invest. 106:1081-1093.

* cited by examiner

*Primary Examiner* — Chang-Yu Wang
(74) *Attorney, Agent, or Firm* — Saul Ewing LLP; Kathryn Doyle

(57) ABSTRACT

The present invention provides methods of treating a subject diagnosed with, or at risk for developing, pathogenic fibrosis, particularly pulmonary fibrosis. The method of the invention comprises administering to the subject a compound or composition which inhibits semaphorin (SEMA) 7A, SEMA 7A receptors, or downstream effectors. A SEMA 7A inhibitor comprises an antibody, a soluble SEMA 7A receptor, an siRNA, a ribozyme, an antisense, an aptamer, a peptidomimetic, a small molecule, a soluble receptor, or any combinations thereof.

15 Claims, 9 Drawing Sheets

(A)

(B)

(C)

(D)

(A)

(B)

(C)

(A)

(B)

SEMAPHORIN 7A PLAYS A CRITICAL ROLE IN TGF-$\beta_1$-INDUCED PULMONARY FIBROSIS AND ALVEOLAR DESTRUCTION

STATEMENT REGARDING FEDERALLY SPONSORED RESEARCH OR DEVELOPMENT

This invention was supported in part by funds obtained from the U.S. Government (National Institutes of Health Grant Numbers HL-56389, HL-064242 and HL-078744), and the U.S. Government has certain rights in the invention.

CROSS-REFERENCE TO RELATED APPLICATIONS

This is a Continuation-In-Part of U.S. application Ser. No. 12/377,940, filed Feb. 18, 2009, which is a National Stage application of PCT International Application No. PCT/US2007/018356, filed Aug. 20, 2007, which in turn claims the benefit pursuant to 35 U.S.C. §119(e) of U.S. Provisional Application No. 60/838,993, filed on Aug. 21, 2006, which is hereby incorporated by reference in its entirety herein.

BACKGROUND OF THE INVENTION

Fibrosis is the abnormal formation of excess fibrous connective tissue in an organ or tissue. Fibrosis is a significant cause of patient morbidity and mortality when it occurs in lung and other organs. This can be seen in the interstitial lung diseases (ILD), including idiopathic pulmonary fibrosis (IPF), scleroderma, radiation-induced pulmonary fibrosis and bleomycin lung, where fibroproliferative matrix molecule deposition, enhanced collagen accumulation, apoptosis and alveolar septal rupture with honeycombing are often juxtaposed and can lead to fatal consequences (Noble et al., 2004, Clin Chest Med. 25:749-758, vii.; Raghu 1998, Interstitial lung disease: a clinical overview and general approach. In Fishman's Pulmonary Diseases and Disorders. Fishman et al., eds., Mc-Graw Hill Inc., N.Y., N.Y. 1037-1053; Selman et al., 2004, Drugs 64:405-430; Thannickal et al., 2006, Proc Am Thorac Soc. 3:350-356). Airway fibrosis is also an important contributor to the pathogenesis of airways disorders such as bronchiolitis obliterans syndrome and asthma (Elias et al., 2003, J Clin Invest. 111:291-297; Elias et al., 1999, J Clin Invest. 104:1001-1006; Hamid, 2003, J Allergy Clin Immunol. 111:1420-1421; Pendergast, 2002, AdvCancer Res. 85:51-100; Vignola et al., 2003, Chest 123:417 S-422S). The mechanisms of tissue fibrosis in these important lung disorders are poorly understood.

The transforming growth factor-beta1 (TGF-$\beta_1$) has been implicated in the pathogenesis of a variety of fibrotic disorders including IPF, scleroderma, radiation induced pulmonary fibrosis and asthma (Leask et al., 2004, FASEB J. 18:816-827; Bergeron et al., 2003, Eur Respir J. 22:69-76; Boxall et al., 2006, Eur Respir J. 27:208-229; Howell et al., 2006, Curr Drug Targets 7:547-565; Khalil et al., 1996, Am J Respir Cell Mol. Biol. 14:131-138; Khalil et al., 2001, Thorax 56:907-915; Martin et al., 2000, Int J Radiat Oncol Biol Phys. 47:277-290; Steen, 2006, Autoimmun Rev. 5:122-124). The TGF-$\beta_1$ family proteins are multi-functional cytokines that play pivotal roles in diverse biologic processes including the regulation of cell growth and survival, cell and tissue differentiation, development, inflammation, immunity, hematopoiesis and tissue remodeling (Leask et al., 2004, supra). TGF-$\beta_1$ is essential for wound healing and stimulates matrix molecule deposition. The important roles that TGF-$\beta_1$ might play in IPF can be seen in human studies that demonstrated that bioactive TGF-$\beta_1$ is expressed in an exaggerated fashion in lungs from patients with IPF (Khalil et al., 1996, supra; Khalil et al., 2001, supra; Daniels et al., 2004, J Clin Invest. 114:1308-1316; Xu et al., 2003, Am J. Physiol Lung Cell Mol. Physiol. 285:L527-539). Animals studies have also demonstrated that TGF-$\beta_1$ is a critical mediator of bleomycin-induced pulmonary fibrosis (Daniels et al., 2004, supra; Nakao et al., 1999, J Clin Invest. 104:5-11; Yehualaeshet et al., 2000, Am J Respir Cell Mol. Biol. 23:204-212) and that high dose adenoviral transfer of TGF-$\beta_1$ causes a progressive fibrotic response in the lung in vivo and an IPF-like disease with fibroblastic foci in an explant culture system (Xu et al., 2003, supra). The mechanisms that TGF-$\beta_1$ uses to mediate these tissue responses, however, have not been adequately defined.

The semaphorins (SEMA) are a large family of phylogenetically conserved, secreted and membrane bound proteins that are divided into eight classes based on sequence similarities and distinct structural features (Pasterkamp et al., 2003a, Curr Opin Neurobiol. 13:79-89; Pasterkamp et al., 2003b, Nature 424:398-405). Members of this family act as axon guidance molecules, and SEMA abnormalities have been implicated in the pathogenesis of neurologic disorders such as Alzheimer's and motor neuron degeneration (Pasterkamp et al., 2003a, supra; Pasterkamp et al., 2003b, supra). SEMA are also expressed on myeloid and lymphoid cells including B cells, T cells, NK cells and macrophages and have been implicated in immune responses and the regulation of organogenesis, angiogenesis, apoptosis and neoplasia (Pasterkamp et al., 2003a, supra; Pasterkamp et al., 2003b, supra; Czopik et al., 2006, Immunity 24:591-600; Delorme et al., 2005, Biol Cell 97:589-597; Holmes et al., 2002, Scand J. Immunol. 56:270-275).

SEMA 7A, also called CDw108, was originally discovered based on sequence similarities with the vaccinia virus SEMA homologue A39R and is now known to be the homolog of a number of viral semaphorins (Comeau et al., 1998, Immunity 8:473-482; Comeau et al., 1998, Immunity 8:473-482; Xu et al., 1998, J Biol. Chem. 273:22428-22434; Lange et al., 1998, Genomics 51:340-350; Delorme et al., 2005, supra). SEMA 7A is unique amongst SEMA because it is stabilized via a glycosylphosphatidylinositol (GPI) membrane linkage (Pasterkamp et al., 2003a, supra; Pasterkamp et al., 2003b, supra; Czopik et al., 2006, supra; Xu et al., 1998, supra). In addition, unlike many SEMA, which act as repulsive axonal guidance clues, SEMA 7A enhances central and peripheral axonal growth and is required for proper axon track formation during embryonic development (Pasterkamp et al., 2003a, supra; Pasterkamp et al., 2003b, supra). SEMA 7A may also play prominent roles in inflammation, immunity and dental and osseous tissue responses based on its ability to stimulate macrophage chemotaxis and cytokine production and inhibit T cell function and its expression on ondontoblasts, stimulation of osteoblast migration and regulation of osteoclast fusion (Czopik et al., 2006, supra; Delorme et al., 2005, supra; Holmes et al., 2002, supra; Moresco et al., 2005, J. Neurosci. 25:6105-6118). The effects of SEMA 7A are thought to be mediated via at least two receptors, plexin $C_1$ and beta1 integrin subunits (Pendergast, 2002, Adv Cancer Res. 85:51-100; Pasterkamp et al., 2003b, supra; Delorme et al., 2005, supra). To date, there is no evidence that SEMA 7A play a pathogenic role in fibrosis.

There exists a need for a better molecular understanding of tissue fibrosis in general, and in pulmonary disorders in particular. Further, there is a need in the art for a therapy for treating or alleviating fibrosis. The present invention addresses and meets these needs.

BRIEF SUMMARY OF THE INVENTION

In one embodiment, the present invention comprises a method of inhibiting fibrosis in a mammal at risk of developing fibrosis, the method comprising administering a therapeutically effective amount of a semaphorin 7A (SEMA 7A) inhibitor to a subject, wherein the inhibitor prevents cellular DNA damage and apoptosis thereby inhibiting fibrosis in a subject. In one aspect, the fibrosis comprises pulmonary fibrosis. In another aspect, the fibrosis comprises a pulmonary pathology selected from the list consisting of interstitial lung disease, idiopathic pulmonary fibrosis, scleroderma, radiation-induced pulmonary fibrosis, and bleomycin lung. In still another aspect, the fibrosis comprises any pulmonary disorder wherein at least one of fibroproliferative matrix molecule deposition, enhanced pathological collagen accumulation, apoptosis and alveolar septal rupture with honeycombing occurs. In yet another aspect, the pulmonary fibrosis is TGF-$\beta_1$-induced.

In one aspect, the SEMA 7A inhibitor comprises an antibody, a soluble SEMA 7A receptor, an siRNA, a ribozyme, an antisense, an aptamer, a peptidomimetic, a small molecule, a soluble receptor, or any combinations thereof. In another aspect, the antibody comprises an antibody selected from a polyclonal antibody, a monoclonal antibody, a humanized antibody, a synthetic antibody, a heavy chain antibody, a human antibody, and a biologically active fragment of an antibody. In still another aspect, the biologically active fragment is a Fab fragment, and a F(ab')$_2$ fragment, and combinations thereof. In yet another aspect, the heavy chain antibody is selected from the group consisting of a camelid antibody, a heavy chain disease antibody, and a variable heavy chain immunoglobulin. In still another aspect, the antibody specifically binds to SEMA 7A, a SEMA 7A receptor, a SEMA 7A downstream effector, or a functional fragment thereof. In yet another aspect, the mammal is a human.

In another embodiment, the present invention comprises a method of inhibiting fibrosis in a mammal diagnosed with a disease or disorder involving fibrosis, the method comprising administering a therapeutically effective amount of a SEMA 7A inhibitor to a subject, wherein the inhibitor prevents cellular DNA damage and apoptosis thereby inhibiting fibrosis in a subject. In one aspect, the fibrosis comprises pulmonary fibrosis. In another aspect, the fibrosis comprises a pulmonary pathology selected from the list consisting of interstitial lung disease, idiopathic pulmonary fibrosis, scleroderma, radiation-induced pulmonary fibrosis, and bleomycin lung. In another aspect, the fibrosis comprises any pulmonary disorder wherein at least one of fibroproliferative matrix molecule deposition, enhanced pathological collagen accumulation, apoptosis and alveolar septal rupture with honeycombing occurs. In yet another aspect, the pulmonary fibrosis is TGF-$\beta_1$-induced.

In one aspect, the SEMA 7A inhibitor comprises an antibody, a soluble SEMA 7A receptor, an siRNA, a ribozyme, an antisense, an aptamer, a peptidomimetic, a small molecule, a soluble receptor, or any combinations thereof. In another aspect, the antibody comprises an antibody selected from a polyclonal antibody, a monoclonal antibody, a humanized antibody, a synthetic antibody, a heavy chain antibody, a human antibody, and a biologically active fragment of an antibody, wherein the biologically active fragment is a Fab fragment, and a F(ab')$_2$ fragment, and combinations thereof. In still another aspect, the heavy chain antibody is selected from the group consisting of a camelid antibody, a heavy chain disease antibody, and a variable heavy chain immunoglobulin. In yet another aspect, the antibody specifically binds to SEMA 7A, a SEMA 7A receptor, a SEMA 7A downstream effector, or functional fragments thereof. In still another aspect, the mammal is a human.

In still another embodiment, the present invention comprises a method of inhibiting alveolar remodeling in a mammal diagnosed with a disease or disorder involving fibrosis, the method comprising administering a therapeutically effective amount of a SEMA 7A inhibitor to a subject, wherein the inhibitor prevents cellular DNA damage and apoptosis thereby inhibiting alveolar remodeling and fibrosis in a subject. In one aspect, the fibrosis comprises pulmonary fibrosis. In another aspect, the fibrosis comprises a pulmonary pathology selected from the list consisting of interstitial lung disease, idiopathic pulmonary fibrosis, scleroderma, radiation-induced pulmonary fibrosis, and bleomycin lung. In still another aspect, the fibrosis comprises any pulmonary disorder wherein at least one of fibroproliferative matrix molecule deposition, enhanced pathological collagen accumulation, apoptosis and alveolar septal rupture with honeycombing occurs. In yet another aspect, the pulmonary fibrosis is TGF-$\beta_1$-induced.

In one aspect, the SEMA 7A inhibitor comprises an antibody, a soluble SEMA 7A receptor, an siRNA, a ribozyme, an antisense, an aptamer, a peptidomimetic, a small molecule, a soluble receptor, or any combinations thereof. In another aspect, the antibody comprises an antibody selected from a polyclonal antibody, a monoclonal antibody, a humanized antibody, a synthetic antibody, a heavy chain antibody, a human antibody, and a biologically active fragment of an antibody, wherein the biologically active fragment is a Fab fragment, and a F(ab')$_2$ fragment, and combinations thereof. In still another aspect, the heavy chain antibody is selected from the group consisting of a camelid antibody, a heavy chain disease antibody, and a variable heavy chain immunoglobulin. In yet another aspect, the antibody specifically binds to SEMA 7A, a SEMA 7A receptor, a SEMA 7A downstream effector, or functional fragments thereof. In still another aspect, the mammal is human.

In yet another embodiment, the present invention comprises a method of inhibiting lung epithelial cell apoptosis in a mammal diagnosed with a disease or disorder involving fibrosis, said method comprising administering a therapeutically effective amount of a SEMA 7A inhibitor to said subject, wherein said inhibitor prevents cellular DNA damage thereby inhibiting lung epithelial cell apoptosis in said subject. In one aspect of the invention, the SEMA 7A inhibitor comprises an antibody, a soluble SEMA 7A receptor, an siRNA, a ribozyme, an antisense, an aptamer, a peptidomimetic, a small molecule, a soluble receptor, or any combinations thereof. In another aspect, the antibody comprises an antibody selected from a polyclonal antibody, a monoclonal antibody, a humanized antibody, a synthetic antibody, a heavy chain antibody, a human antibody, and a biologically active fragment of an antibody, wherein the biologically active fragment is a Fab fragment, and a F(ab')$_2$ fragment, and combinations thereof. In still another aspect, the heavy chain antibody is selected from the group consisting of a camelid antibody, a heavy chain disease antibody, and a variable heavy chain immunoglobulin. In yet another aspect, the antibody specifically binds to SEMA 7A, a SEMA 7A receptor, a SEMA 7A downstream effector, or functional fragments thereof. In yet another aspect, the mammal is human.

In yet another embodiment, the present invention comprises a method of inhibiting pathological collagen deposition in lung of a mammal, the method comprising administering a therapeutically effective amount of a SEMA 7A inhibitor to the mammal, wherein the inhibitor prevents pathological collagen deposition. In one aspect of the invention, the SEMA 7A inhibitor comprises an antibody, a soluble SEMA 7A receptor, an siRNA, a ribozyme, an antisense, an aptamer, a peptidomimetic, a small molecule, a soluble receptor, or any combinations thereof. In another aspect, the antibody comprises an antibody selected from a polyclonal antibody, a monoclonal antibody, a humanized antibody, a synthetic antibody, a heavy chain antibody, a human antibody, and a biologically active fragment of an antibody, wherein the biologically active fragment is a Fab fragment, and a F(ab')$_2$ fragment, and combinations thereof. In still another aspect, the heavy chain antibody is selected from the group consisting of a camelid antibody, a heavy chain disease antibody, and a variable heavy chain immunoglobulin. In yet another aspect, the antibody specifically binds to SEMA 7A, a SEMA 7A receptor, and a SEMA 7A downstream effector, or functional fragments thereof. In yet another aspect, the mammal is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2A is a series of representative images of lung sections subjected to trichrome staining for histologic analysis. FIG. 2B depicts total collagen data from sirchol collagen assays. FIG. 2C is a series of representative images of lung sections stained with H&E for histologic analysis.

FIG. 3A is a series of representative images of lung sections subjected to TUNEL staining. Arrows highlight representative TUNEL staining cells. FIG. 3B is a bar graph of data from TUNEL evaluations. The values in Figure B represent the mean±SEM of evaluations in a minimum of 5 mice (*p<0.011, **p<0.001). FIG. 3C is an image of a Western blot of lung lysates to examine caspase-mediated ICAD cleavage. FIGS. 3A and 3C are representative of at least 5 similar experiments.

FIG. 4A is a bar graph depicting the levels of total (solid squares) and activated (open squares) TGF-$\beta_1$ in BAL fluids from the mice evaluated by ELISA. FIG. 4B is an image of a Western blot analysing the levels of total and phosphorylated Smads 2 and 3. FIG. 4B is representative of 4 similar evaluations. FIG. 4C is a bar graph of the levels of mRNA encoding Smad 7 quantitated by real time RT-PCR. The values in FIGS. 4A and 4C represent the mean±SEM of evaluations in a minimum of 5 mice. (N.S.=not significant; *p<0.01).

FIG. 8A is a representative image of lung section subjected to tissue trichrome stain for histologic analysis. The data are representative of 5 similar experiments. FIG. 8B is a graph of total collagen data from sirchol collagen assays. The data represent the mean±SEM of evaluations in a minimum of 5 mice (*p<0.01, **p<0.001).

DETAILED DESCRIPTION OF THE INVENTION

Figure 1:
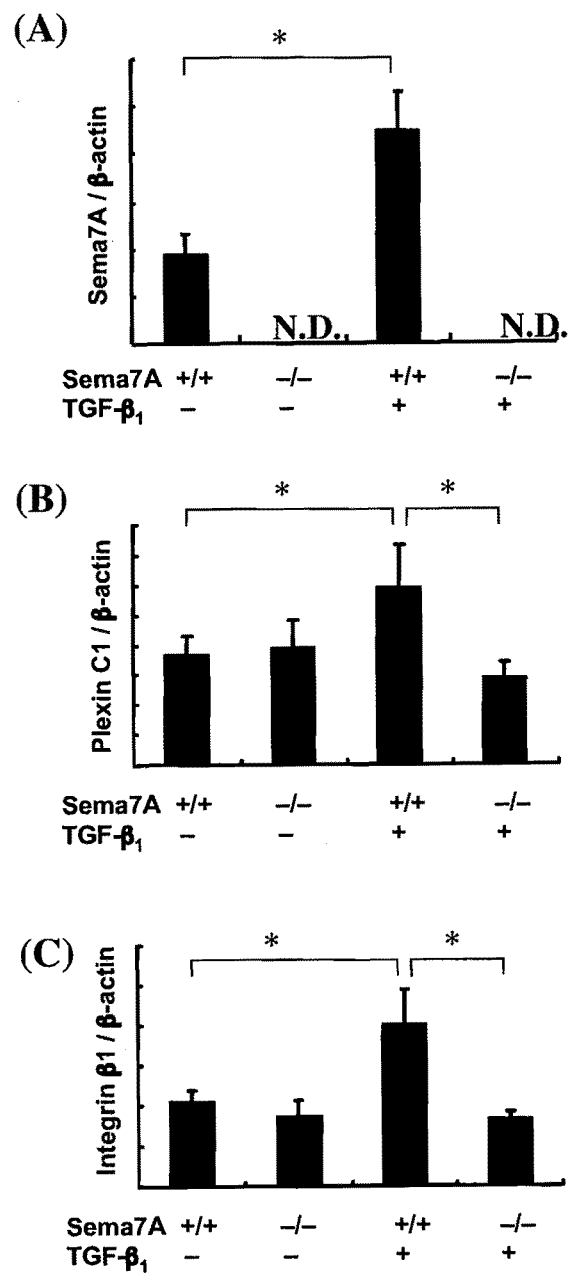
FIGS. 1A-1C are bar graphs relating to the regulation of SEMA 7A and its receptors by TGF-$\beta_1$ Tg (−) and Tg (+) mice with wild type (+/+) and null (−/−) SEMA 7A loci were generated. The levels of mRNA encoding SEMA 7A (FIG. 1A), Plexin-C1 (FIG. 1B) and B 1 integrins (FIG. 1C) were evaluated in these mice using real time-RT-PCR after 2 weeks of transgene activation. The noted values represent the mean±SEM of evaluations in a minimum of 5 mice (*p<0.001, N.D.=none detected).

The present invention uses inhibitors of SEMA 7A, SEMA 7A receptors and SEMA 7A downstream effectors to prevent, treat or reverse TGF $\beta_1$ induced DNA injury, cellular apoptosis, pathological deposition of collagen, alveolar remodeling and fibrosis pathogenesis.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"Alveolar remodeling" refers to one or more changes in alveolar cells observed in various pulmonary diseases and disorders, including, but not limited to, pulmonary epithelial cell DNA destruction, apoptosis, pathological accumulation of collagen, alveolar honeycombing, and alveolar septal destruction.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, the term "heavy chain antibody" or "heavy chain antibodies" comprises immunoglobulin molecules derived from camelid species, either by immunization with an antigen and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator," as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

Signal transduction is any process by which a cell converts one signal or stimulus into another, most often involving ordered sequences of biochemical reactions carried out within the cell. The number of proteins and molecules participating in these events increases as the process eminates from the initial stimulus resulting in a "signal cascade." The phrase "downstream effector", as used herein, refers to a protein or molecule acted upon during a signaling cascade, which in term acts upon another protein or molecule. The term "downstream" indicates the direction of the signaling cascade.

A disease or disorder is "alleviated" if the severity of a symptom of the disease, or disorder, the frequency with which such a symptom is experienced by a patient, or both, are reduced.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "recombinant DNA" as used herein is defined as DNA produced by joining pieces of DNA from different sources.

The term "recombinant polypeptide" as used herein is defined as a polypeptide produced by using recombinant DNA methods.

"Ribozymes" as used herein are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules. Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053).

By the term "specifically binds," as used herein, is meant a molecule, such as an antibody, which recognizes and binds to another molecule or feature, but does not substantially recognize or bind other molecules or features in a sample.

As used herein, the term "transdominant negative mutant gene" refers to a gene encoding a protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The phrase "SEMA 7A inhibitor," as used herein, refers to a composition or compound that inhibits semaphorin 7A activity, either directly or indirectly, using any method known to the skilled artisan. A SEMA 7A inhibitor may be any type of compound, including but not limited to, a polypeptide, a nucleic acid, an aptamer, a peptidometic, and a small molecule.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

It is understood that any and all whole or partial integers between any ranges set forth herein are included herein.

DESCRIPTION

The invention springs in part from the discovery that TGF-$\beta_1$ is a potent stimulator of SEMA 7A and SEMA 7A receptors, such as plexin $C_1$ and beta1 integrin subunits. Specifically, it has been discovered that SEMA 7A plays a key role in the pathogenesis of TGF-$\beta_1$-induced fibrosis and alveolar remodeling and that TGF-$\beta_1$ regulates the expression of SEMA 7A receptors, extracellular matrix (ECM) proteins, proteases, anti-proteases, transcription factors, fibrogenetic cytokines, apoptosis regulators and IL-13 receptors via Smad 2/3-independent, SEMA 7A-dependent activation pathways. Importantly, the present invention demonstrates that SEMA 7A is not a major regulator of TGF-$\beta_1$-induced inflammation in the lung, but is an important contributor to TGF-$\beta_1$-induced DNA injury and apoptosis of pulmonary epithelial cells in the lung as well as the pathological accumulation of collagen. It has also been demonstrated that SEMA 7A plays a role in the pathogenesis of fibrosis induced by bleomycin, suggesting the role of SEMA 7A in fibrosis pathogenesis is independent of the origin of fibrosis.

Accordingly, the invention provides a method of inhibiting fibrosis in a subject diagnosed with a disease or disorder involving fibrosis or in a subject at risk of developing fibrosis. The invention further provides a method of inhibiting lung epithelial cell DNA injury and apoptosis, a method of inhibiting the pathological deposition of collagen, and a method of inhibiting alveolar remodeling in a subject diagnosed with, or at risk of developing, a disease or disorder involving fibrosis. The methods of the invention comprise administering a therapeutically effective amount of a semaphorin 7A inhibitor to the subject wherein the inhibitor reduces or prevents cellular DNA injury, apoptosis, and pathological deposition of collagen. The methods of the invention further comprise administering a therapeutically effective amount of a semaphorin 7A inhibitor to a subject wherein alveolar remodeling and fibrosis is prevented, halted, or reversed.

The invention may be practiced in any subject diagnosed with, or at risk of developing, fibrosis. Fibrosis is associated with many diseases and disorders. Preferably, the fibrosis is pulmonary fibrosis. The subject may be diagnosed with, or at risk for developing interstitial lung disease including idiopathic pulmonary fibrosis, scleroderma, radiation-induced pulmonary fibrosis, bleomycin lung, sarcoidosis, silicosis, familial pulmonary fibrosis, an autoimmune disease or any disorder wherein one or more fibroproliferative matrix molecule deposition, enhanced pathological collagen accumulation, apoptosis and alveolar septal rupture with honeycombing occurs. The subject may be identified as having fibrosis or being at risk for developing fibrosis because of exposure to asbestos, ground stone and metal dust, or because of the administration of a medication, such as bleomycin, busulfon, pheytoin, and nitro furantoin, which are risk factors for developing fibrosis. Preferably, the subject is a mammal and more preferably, a human. It is also contemplated that the compositions and methods of the invention may be used in the treatment of organ fibrosis secondary to allogenic organ transplant, e.g., graft transplant fibrosis. Non-limiting examples include renal transplant fibrosis, heart transplant fibrosis, liver transplant fibrosis, etc.

Inhibiting SEMA 7A activity can be accomplished using any method known to the skilled artisan. Examples of methods to inhibit SEMA 7A activity include, but are not limited to decreasing expression of an endogenous SEMA 7A gene, decreasing expression of SEMA 7A mRNA, and inhibiting activity of SEMA 7A protein. A SEMA 7A inhibitor may therefore be a compound or composition that decreases expression of a SEMA 7A gene, a compound or composition that decreases SEMA 7A mRNA half-life, stability and/or expression, or a compound or composition that inhibits SEMA 7A protein function. A SEMA 7A inhibitor may be any type of compound, including but not limited to, a polypeptide, a nucleic acid, an aptamer, a peptidometic, and a small molecule, or combinations thereof.

SEMA 7A inhibition may be accomplished either directly or indirectly. For example, SEMA 7A may be directly inhibited by compounds or compositions that directly interact with SEMA 7A protein, such as antibodies or soluble SEMA 7A receptors. Alternatively, SEMA 7A may be inhibited indirectly by compounds or compositions that inhibit SEMA 7A receptors, SEMA 7A downstream effectors, or upstream regulators which up-regulate SEMA 7A expression.

Decreasing expression of an endogenous SEMA 7A gene includes providing a specific inhibitor of SEMA 7A gene expression. Decreasing expression of SEMA 7A mRNA or SEMA 7A protein includes decreasing the half-life or stability of SEMA 7A mRNA or decreasing expression of SEMA 7A mRNA. Methods of decreasing expression of SEMA 7A include, but are not limited to, methods that use an siRNA, a microRNA, an antibody, a soluble receptor, an antisense nucleic acid, a ribozyme, an expression vector encoding a transdominant negative mutant, a peptide, a small molecule, other specific inhibitors of SEMA 7A gene, mRNA, and protein expression, and combinations thereof.

Methods of Inhibiting SEMA 7A, SEMA 7A Receptor, and Downstream Effector Protein: Antibodies In one embodiment of the invention, the semaphorin 7A (SEMA 7A) inhibitor is an antibody. It will be appreciated by one skilled in the art that an antibody comprises any immunoglobulin molecule, whether derived from natural sources or from recombinant sources, which is able to specifically bind to an epitope present on a target molecule. In the present invention, the target molecule may be SEMA 7A, a SEMA 7A receptor, a SEMA 7A downstream effector, or fragments thereof. In one aspect of the invention, SEMA 7A is directly inhibited by an antibody that specifically binds to an epitope on SEMA 7A. In another aspect of the invention, SEMA 7A is indirectly inhibited by an antibody that specifically binds to an epitope on a SEMA 7A receptor, such as plexin $C_1$ or a beta1 integrin subunit. In yet another aspect of the invention, the effects of SEMA 7A are blocked by an antibody that specifically binds to an epitope on a downstream effector such as extracellular matrix (ECM) proteins, proteases, anti-proteases, transcription factors, fibrogenetic cytokines, apoptosis regulators and IL-13 receptor components.

When the SEMA 7A inhibitor used in the compositions and methods of the invention is a polyclonal antibody (IgG), the antibody is generated by inoculating a suitable animal with a peptide comprising full length SEMA 7A (SEQ ID NO.: 2), a SEMA 7A receptor (GenBank Accession Nos.: NM_005761 and P05556), a SEMA 7A downstream effector, or fragments thereof. These polypeptides, or fragments thereof, may be obtained by any method known in the art, including chemical synthesis and biological synthesis, as described elsewhere herein. In this regard, an exemplary human SEMA 7A sequence is SEQ ID NO.: 2. Antibodies produced in the inoculated animal which specifically bind to SEMA 7A, a SEMA 7A receptor, a SEMA 7A downstream effector, or fragments thereof, are then isolated from fluid obtained from the animal. Antibodies may be generated in this manner in several non-human mammals such as, but not limited to goat, sheep, horse, camel, rabbit, and donkey. Methods for generating polyclonal antibodies are well known in the art and are described, for example in Harlow, et al. (1988, In: Antibodies, A Laboratory Manual, Cold Spring Harbor, N.Y.).

Monoclonal antibodies directed against a full length SEMA 7A, a SEMA 7A receptor, a SEMA 7A downstream effector, or fragment thereof, may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Human monoclonal antibodies may be prepared by the method described in U.S. patent publication 2003/0224490. Monoclonal antibodies directed against an antigen are generated from mice immunized with the antigen using standard procedures as referenced herein. Nucleic acid encoding the monoclonal antibody obtained using the procedures described herein may be cloned and sequenced using technology which is available in the art, and is described, for example, in Wright et al. (1992, Critical Rev. in Immunol. 12(3, 4):125-168) and the references cited therein.

When the antibody used in the methods of the invention is a biologically active antibody fragment or a synthetic antibody corresponding to antibody to a full length SEMA 7A, a SEMA 7A receptor, a SEMA 7A downstream effector, or fragments thereof, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology which is available in the art, and described, for example, in Wright et al. (1992, Critical Rev. in Immunol. 12(3, 4):125-168) and the references cited therein. Alternatively, quantities of the desired antibody or fragment thereof may also be synthesized using chemical synthesis technology. If the amino acid sequence of the antibody is known, the desired antibody can be chemically synthesized using methods known in the art as described elsewhere herein.

The present invention also includes the use of humanized antibodies specifically reactive with an epitope present on a target molecule. These antibodies are capable of binding to the target molecule. The humanized antibodies useful in the invention have a human framework and have one or more complementarity determining regions (CDRs) from an antibody, typically a mouse antibody, specifically reactive with a targeted cell surface molecule.

When the antibody used in the invention is humanized, the antibody can be generated as described in Queen, et al. (U.S. Pat. No. 6,180,370), Wright et al., (supra) and in the references cited therein, or in Gu et al. (1997, Thrombosis and Hematocyst 77(4):755-759), or using other methods of generating a humanized antibody known in the art. The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to humanized immunoglobulin coding sequences, including naturally-associated or heterologous promoter regions. The expression control sequences can be eukaryotic promoter systems in vectors capable of transforming or transfecting eukaryotic host cells, or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO 87/02671. CDRs useful in producing the antibodies of the present invention may be similarly derived from DNA encoding monoclonal antibodies capable of binding to the target molecule. Such humanized antibodies may be generated using well known methods in any convenient mammalian source capable of producing antibodies, including, but not limited to, mice, rats, camels, llamas, rabbits, or other vertebrates. Suitable cells for constant region and framework DNA sequences and host cells in which the antibodies are expressed and secreted, can be obtained from a number of sources, such as the American Type Culture Collection, Manassas, Va.

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies are useful in that they are smaller than conventional mammalian antibodies, they are more soluble than conventional antibodies, and further demonstrate an increased stability compared to some other antibodies. Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species. As an example, the production of antibodies in mammals is detailed in such references as Harlow et al., (1988, Antibodies: A Laboratory Manual, Cold Spring Harbor, N.Y.).

$V_H$ proteins isolated from other sources, such as animals with heavy chain disease (Seligmann et al., 1979, Immunological Rev. 48:145-167, incorporated herein by reference in its entirety), are also useful in the compositions and methods of the invention. The present invention further comprises variable heavy chain immunoglobulins produced from mice and other mammals, as detailed in Ward et al. (1989, Nature 341:544-546, incorporated herein by reference in its entirety). Briefly, $V_H$ genes are isolated from mouse splenic preparations and expressed in *E. coli*. The present invention encompasses the use of such heavy chain immunoglobulins in the compositions and methods detailed herein.

Antibodies useful as SEMA 7A inhibitors in the invention may also be obtained from phage antibody libraries. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes, "Protein Purification", Springer-Verlag, N.Y. (1982)). Substantially pure antibodies of at least about 90% to 95% homogeneity are preferred, and antibodies having 98% to 99% or more homogeneity most preferred for pharmaceutical uses. Once purified, the antibodies may then be used to practice the method of the invention, or to prepare a pharmaceutical composition useful in practicing the method of the invention.

The antibodies of the present invention can be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g, Current Protocols in Molecular Biology, (Ausubel et al., eds.), Greene Publishing Associates and Wiley-Interscience, New York (2002)). Exemplary immunoassays are described briefly below (but are not intended to be in any way limiting).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 14 hours) at 4.degree. C., adding protein A and/or protein G sepharose beads to the cell lysate, incubating for about an hour or more at 4.degree. C., washing the beads in lysis buffer and resuspending the beads in SDS/sample buffer. The ability of the antibody of interest to immunoprecipitate a particular antigen can be assessed by, e.g., western blot analysis. Those of ordinary skill in the art will be knowledgeable as to the parameters that can be modified to increase the binding of the antibody to an antigen and decrease the background (e.g., pre-clearing the cell lysate with sepharose beads), upon consideration of the present disclosure. Additional immunoprecipitation protocols are presented Current Protocols in Molecular Biology, (Ausubel et al., eds.), Greene Publishing Associates and Wiley-Interscience, New York (2002).

Western blot analysis generally comprises preparing protein samples, electrophoresis of the protein samples in a polyacrylamide gel (e.g., about 8 20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with about 3% BSA or non-fat milk), washing the membrane in washing buffer (e.g., PBS-TWEEN 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., .sup.32P or .sup.125I) diluted in blocking buffer, washing the membrane in wash buffer, and detecting the presence of the antigen. Those of ordinary skill in the art will be knowledgeable as to the parameters that can be modified to increase the signal detected and to reduce the background noise, upon consideration of the present disclosure. Additional western blot protocols are presented in Current Protocols in Molecular Biology, (Ausubel et al., eds.), Greene Publishing Associates and Wiley-Interscience, New York (2002).

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. When performing an ELISA, the antibody of interest does not need to be conjugated to a detectable compound; instead, a second antibody (which recognizes the antibody of interest) conjugated to a detectable compound can be added to the well. Further, instead of coating the well with the antigen, the antibody may be coated to the well. In this case, a second antibody conjugated to a detectable compound can be added following the addition of the antigen of interest to the coated well. One of ordinary skill in the art will be knowledgeable as to the parameters that can be modified to increase the signal detected as well as other variations of ELISA protocols known in the art. For further discussion regarding ELISA protocols see, e.g., Current Protocols in Molecular Biology, (Ausubel et al., eds.), Greene Publishing Associates and Wiley-Interscience, New York (2002).

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Soluble Receptors

In another embodiment of the invention, soluble SEMA 7A receptor protein (sSEMA 7A-R) that binds to SEMA 7A is contemplated as an inhibitor of SEMA 7A. This agent can be used to reduce or prevent the binding of SEMA 7A to cell bound SEMA 7A-R and thereby act as an antagonist of SEMA 7A. Soluble receptors have been used to bind cytokines or other ligands to regulate their function (Thomson, (1998) Cytokine Handbook, Academic Press). A soluble receptor occurs in solution, or outside of the membrane. Soluble receptors may occur because the segment of the molecule which spans or associates with the membrane is absent. This segment is commonly referred to in the art as the transmembrane domain of the gene, or membrane binding segment of the protein. Thus, in some embodiments of the invention, a soluble receptor includes a fragment or an analog of a membrane bound receptor. Preferably, the fragment contains at least six, e.g., ten, fifteen, twenty, twenty-five, thirty, forty, fifty, sixty, or seventy amino acids, provided it retains its desired activity.

In other embodiments of the invention, the structure of the segment that associates with the membrane is modified (e.g., DNA sequence polymorphism or mutation in the gene) so the receptor is not tethered to the membrane, or the receptor is inserted, but is not retained within the membrane. Thus, a soluble receptor, in contrast to the corresponding membrane bound form, differs in one or more segments of the gene or receptor protein that are important to its association with the membrane.

The present invention encompasses cDNA encoding a soluble SEMA-7A receptor protein which is isolated from SEMA 7A-R producing cells or is recombinantly engineered from SEMA 7A-R-encoding DNA. Soluble SEMA 7A-R, as used herein, refers to a protein which can specifically bind to SEMA 7A without eliciting undesired downstream effects including, but not limited to, pulmonary epithelial cell DNA destruction, apoptosis, pathological collagen deposition, and alveolar remodeling.

SEMA 7A receptors known in the art include human plexin $C_1$, (GenBank Accession No.: NM_005761) and human $\beta_1$ integrin (GenBank Accession No.: P05556). However, the invention should not be considered to be limited to the use of these receptors. Any SEMA 7A receptor identified may serve as the basis for the generation of a soluble SEMA 7A receptor.

Any of a variety of procedures may be used to molecularly clone soluble SEMA 7A-R (sSEMA 7A-R) cDNA. These methods include, but are not limited to, direct functional expression of the sSEMA 7A-R gene following the construction of an sSEMA 7A-R-containing cDNA library in an appropriate expression vector system.

It is readily apparent to those skilled in the art that suitable cDNA libraries may be prepared from cells or cell lines which have SEMA 7A-R activity. The selection of cells or cell lines for use in preparing a cDNA library to isolate SEMA 7A-R cDNA may be done by first measuring SEMA 7A-R activity using a SEMA 7A binding assay.

Preparation of cDNA Libraries can be Performed by Standard Techniques Well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding SEMA 7A-R may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manuel (Cold Spring Harbor Laboratory, Cold Spring Harbor, N.Y., 1982).

sSEMA 7A-R molecules may also be obtained by recombinantly engineering them from DNA encoding the partial or complete amino acid sequence of a SEMA 7A-R. Using recombinant DNA techniques, DNA molecules are constructed which encode at least a portion of the SEMA 7A receptor capable of binding SEMA 7A without stimulating pulmonary endothelial cell DNA destruction, apoptosis, pathological collagen deposition, and alveolar remodeling. Standard recombinant DNA techniques are used such as those found in Maniatis, et al., supra.

DNA encoding sSEMA 7A-R is constructed from a DNA sequence encoding a SEMA 7A receptor. For purposes of illustration, DNA encoding the SEMA 7A-R plexin C1 is utilized. Using the receptor DNA sequence, a DNA molecule is constructed which encodes the extracellular domain of the receptor, or the SEMA 7A binding domain only and is denoted sSEMA 7A-R. Restriction endonuclease cleavage sites are identified within the receptor DNA and can be utilized directly to excise the extracellular-encoding portion. In addition, PCR techniques well known in the art may be utilized to produce the desired portion of DNA. It is readily apparent to those skilled in the art that other techniques, which are standard in the art, may be utilized to produce sSEMA 7A-R molecules in a manner analogous to those described above. Such techniques are found, for example, in Maniatis et al., supra.

The cloned sSEMA 7A-R cDNA obtained through the methods described above may be recombinantly expressed by molecular cloning into an expression vector containing a suitable promoter and other appropriate transcription regulatory elements, and transferred into prokaryotic or eukaryotic host cells to produce recombinant sSEMA 7A-R. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, fungal cells, yeast cells, plant cells, insect cells and animal cells.

Specifically designed vectors allow the shuttling of DNA between hosts such as bacteria-yeast or bacteria-animal or bacteria-insect cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant sSEMA 7A-R in mammalian cells. Commercially available mammalian expression vectors which may be suitable for recombinant sSEMA 7A-R expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMT-neo(342-12) (ATCC 37224), pRSVgpt (ATCC 37199), pRS-Vneo (ATCC 37198), pSV2-dhfr (ATCC 37146), pUCTag (ATCC 37460), and gZD35 (ATCC 37565).

DNA encoding sSEMA 7A-R may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila, moth, mosquito and armyworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171). Insect cell lines which may be suitable and are commercially available include but are not limited to 3M-S (ATCC CRL 8851) moth (ATCC CCL 80) mosquito (ATCC CCL 194 and 195; ATCC CRL 1660 and 1591) and armyworm (Sf9, ATCC CRL 1711).

The expression vector may be introduced into host cells via any one of a number of techniques including but not limited to transformation, transfection, liposome or protoplast fusion, and electroporation. The expression vector-containing cells are clonally propagated and individually analyzed to determine whether they produce sSEMA 7A-R protein. Identification of sSEMA 7A-R expressing host cell clones may be done by several means, including but not limited to immunological reactivity with anti-sSEMA 7A-R antibodies, binding to radiolabelled SEMA 7A, and the presence of host cell-secreted sSEMA 7A-R activity.

Expression of sSEMA 7A-R DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

Levels of sSEMA 7A-R protein produced by host cells may be quantitated by immunoaffinity and/or ligand affinity techniques. sSEMA 7A-R-specific affinity beads or sSEMA 7A-R-specific antibodies are used to isolate $^{35}$S-methionine labeled or unlabeled sSEMA 7A-R protein. Labeled sSEMA 7A-R protein is analyzed by SDS-PAGE. Unlabeled sSEMA 7A-R protein is detected by Western blotting, ELISA or RIA assays employing sSEMA 7A-R specific antibodies, or by ligand blotting with labeled SEAM 7A.

Following expression of sSEMA 7A-R in a recombinant host cell, sSEMA 7A-R protein may be recovered to provide sSEMA 7A-R in active form, capable of binding SEMA 7A without stimulating lung epithelial cell DNA damage, apoptosis, pathological collagen deposition, and alveolar remodeling. Several sSEMA 7A-R purification procedures are available and suitable for use. sSEMA 7A-R may be purified from cell lysates and extracts, or from conditioned culture medium, by various combinations of, or individual application of salt fractionation, ion exchange chromatography, size exclusion chromatography, hydroxylapatite adsorption chromatography, reversed phase chromatography, heparin sepharose chromatography, sSEMA 7A-R ligand affinity chromatography, and hydrophobic interaction chromatography.

In addition, recombinant sSEMA 7A-R can be separated from other cellular proteins by use of an immuno-affinity column made with monoclonal or polyclonal antibodies specific for full length sSEMA 7A-R, or polypeptide fragments of sSEMA 7A-R. The sSEMA 7A-R protein can be expressed using a baculovirus expression system. The recombinantly produced sSEMA 7A-R is purified from the recombinant host cell extracts or cell culture fluid using heparin-sepharose column chromatography which specifically binds the sSEMA 7A-R protein. The heparin-sepharose bound sSEMA 7A-R column is washed using a suitable buffer containing between b 0.1M and 0.6M NaCl which removes contaminating proteins without significant loss of sSEMA 7A-R. The sSEMA 7A-R is eluted from the heparin-sepharose column using a suitable buffer containing about 1M NaCl, yielding substantially purified sSEMA 7A-R.

siRNA

In one embodiment, siRNA is used to decrease the level of SEMA 7A protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of SEMA 7A protein using RNAi technology.

Modification of siRNA

Following the generation of the siRNA polynucleotide of the present invention, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

Vectors

In other related aspects, the invention includes an isolated nucleic acid encoding an inhibitor, wherein the inhibitor such as an siRNA, inhibits SEMA 7A, a SEMA 7A receptor, a regulator thereof; or a downstream effector, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York). In another aspect of the invention, SEMA 7A, a SEMA 7A receptor, or a regulator thereof, can be inhibited by way of inactivating and/or sequestering SEMA 7A, a SEMA 7A receptor, or a regulator thereof. As such, inhibiting the effects of SEMA 7A can be accomplished by using a trans-dominant negative mutant.

In another aspect, the invention includes a vector comprising an siRNA polynucleotide. Preferably, the siRNA polynucleotide is capable of inhibiting the expression of a target polypeptide, wherein the target polypeptide is selected from the group consisting of SEMA 7A, a SEMA 7A receptor, and a downstream effector, or regulators thereof. The incorporation of a desired polynucleotide into a vector and the choice of vectors is well-known in the art as described in, for example, Sambrook et al., supra, and Ausubel et al., supra.

The siRNA polynucleotide can be cloned into a number of types of vectors. However, the present invention should not be construed to be limited to any particular vector. Instead, the present invention should be construed to encompass a wide plethora of vectors which are readily available and/or well-known in the art. For example, an siRNA polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient endonuclease sites, and one or more selectable markers. (See, e.g., WO 01/96584; WO 01/29058; and U.S. Pat. No. 6,326,193.

For expression of the siRNA, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the siRNA, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of Inhibiting SEMA 7A Gene and mRNA Expression

Antisense Nucleic Acids

In one embodiment of the invention, an antisense nucleic acid sequence which is expressed by a plasmid vector is used to inhibit SEMA 7A, a SEMA 7A receptor, or a SEMA 7A downstream effector expression. The antisense expressing vector is used to transfect a mammalian cell or the mammal itself, thereby causing reduced endogenous expression of SEMA 7A, a SEMA 7A receptor, or a SEMA 7A downstream effector. Examples of downstream effectors include, but are not limited to, extracellular matrix proteins (collagens, fibronectin, elastin, fibrillin), CCN proteins 1-5 (Cyr61, connective tissue growth factor, NOV3, Wisp-1, Wisp-2), fibroblast growth factor-2, IL-13 receptor components, proteases (cathespsins-S, -K, -B, and -H), antiproteases, and apoptosis regulators (Bax, TNF, and early response gene-1).

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262: 40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Ribozymes

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053).

Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit SEMA 7A, a SEMA 7A receptor, or a SEMA 7A downstream effector expression. Ribozymes useful for inhibiting the expression of a target molecule may be designed by incorporating target sequences into the basic ribozyme structure which are complementary, for example, to the mRNA sequence of SEMA 7A of the present invention. Ribozymes targeting SEMA 7A, a SEMA 7A receptor, or a downstream effector thereof, may be synthesized using commercially available reagents (Applied Biosystems, Inc., Foster City, Calif.) or they may be genetically expressed from DNA encoding them.

Assays for Identifying and Testing Candidate Inhibitors of SEMA 7A

Inhibitors of gene expression, mRNA stability and expression, and protein activity, function and expression of SEMA 7A, SEMA 7A receptors, and downstream effectors can be identified by screening test compounds. For instance, inhibitors of endogenous SEMA 7A gene expression or of SEMA 7A mRNA expression can be identified by screening test compounds for their capacity to reduce or preclude SEMA 7A gene expression or SEMA 7A mRNA expression in a cell, preferably a pulmonary endothelial cell. The SEMA 7A coding sequence (SEQ ID NO.: 1) in such screening assays may include an in-frame fusion of a tag to the SEMA 7A coding sequence. Such tags enable monitoring of SEMA 7A expression by antibody detection of the tags or spectral methods of detection (e.g., fluorescence or luminescence).

Test compounds for use in such screening methods can be small molecules, nucleic acids including aptamers, peptides, peptidomimetics and other drugs. Peptide fragments of SEMA 7A are contemplated that can competitively inhibit the binding of SEMA 7A to a cognate receptor, thereby inhibiting SEMA 7A activity. Peptide fragments of SEMA 7A that include the known Arg-Gly-Asp (RGD) β1 integrin binding domain are preferred in the present invention.

The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145). Inhibitors and activators of SEMA 7A expression may be useful in therapeutic applications, or serve as lead drugs in the development of therapeutics. Synthetic techniques may be used to produce compounds, such as: chemical and enzymatic production of small molecules, peptides, nucleic acids, antibodies, and other therapeutic compositions useful in the practice of the methods of the invention. Other techniques may be used which are not described herein, but are known to those of skill in the art.

In one aspect of the invention libraries of small molecules, including but not limited to aptamers, peptidomimetics, SEMA 7A peptide fragments, or peptidomimetics, may be assayed for competitive binding to one or both known SEMA 7A receptors, or any SEMA 7A receptor identified in the future. In another aspect of the invention, TGF-$\beta_1$ induction in the presence of SEMA 7A of at least one relevant downstream gene is assayed in the presence and absence of a test compound. Relevant downstream genes include: collagens (e.g., α1(I), α1(II) and type III collagens, fibronectin (FN), elastin, laminin); protease (e.g., TIMP-1); fibroregulatory cytokines and their receptors (e.g., CCN1 (Cyr-61), CCN2 (connective tissue growth factor; CTGF), CCN3 (NOV), CCN4 (WISP-1) and CCN5 (WISP-2) (FIGS. 7B-7F). and the IL-13 and IL-4 receptor components IL-4Rα and IL-13Rα2). IL-13 mediates its fibrogenic effects, in part, via its ability to activate TGF-$\beta_1$. The present disclosure provides evidence that inhibiting SEMA 7A limits IL-13 induced fibrogenesis. In yet another aspect of the invention, changes in IL-18 expression are assayed in response to administration of a test compound. IL-18 is known to inhibit tissue fibrosis, but as demonstrated elsewhere herein, SEMA 7A inhibits IL-18 production. In still another aspect of the invention, an in vivo assay is performed to assay a stabilization and reduction of alveolar remodeling as a result of administering a SEMA 7A inhibitor.

In another embodiment of the invention, an in vitro binding assay is used to determine binding affinity and dissociation kinetics of potential SEMA 7A inhibitors for SEMA 7A, SEMA 7A receptors, and SEMA 7A downstream effectors. Examples of in vitro binding assays are well known in the art. Standards may be used when testing new agents or compounds or when measuring the various parameters described herein. For example, TGF-$\beta_1$ can be administered to a group or subject as a standard or control against which the effects of a test agent or compound can be compared. In addition, when measuring a parameter, measurement of a standard can include measuring parameters such as SEMA 7A or SEMA 7A concentrations in a tissue or fluid obtained from a subject before the subject is treated with a test compound and the same parameters can be measured after treatment with the test compound. In another aspect of the invention, a standard can be an exogenously added standard which is an agent or compound that is added to a sample and is useful as an internal control, especially where a sample is processed through several steps or procedures and the amount of recovery of a marker of interest at each step must be determined. Such exogenously added internal standards are often added in a labeled form, i.e., a radioactive isotope.

SEMA 7A inhibitors useful in the invention may be obtained using standard methods known to the skilled artisan. Such methods include chemical organic synthesis or biological means. Biological means include purification from a biological source, recombinant synthesis and in vitro translation systems, using methods well known in the art.

A peptide may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purities, i.e., purities sufficient for research, diagnostic or therapeutic purposes.

Solid phase peptide synthesis is described by Stewart et al. in Solid Phase Peptide Synthesis, 2nd Edition, 1984, Pierce Chemical Company, Rockford, Ill.; and Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group, such as formation into a carbodiimide, a symmetric acid anhydride, or an "active ester" group, such as hydroxybenzotriazole or pentafluorophenyl esters.

Examples of solid phase peptide synthesis methods include the BOC method, which utilizes tert-butyloxycarbonyl as the α-amino protecting group, and the FMOC method, which utilizes 9-fluorenylmethyloxycarbonyl to protect the α-amino of the amino acid residues. Both methods are well-known by those of skill in the art.

Incorporation of N— and/or C— blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB (divinylbenzene), resin, which upon hydrofluoric acid (HF) treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by trifluoroacetic acid (TFA) in dicholoromethane. Esterification of the suitably activated carboxyl function, e.g. with dicyclohexylcarbodiimide (DCC), can then proceed by addition of the desired alcohol, followed by de-protection and isolation of the esterified peptide product.

Incorporation of N-terminal blocking groups may be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product may then be cleaved from the resin, de-protected and subsequently isolated.

Prior to its use as a SEMA 7A inhibitor in accordance with the invention, a peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate polypeptides based on their charge. Affinity chromatography is also useful in purification procedures.

Antibodies and peptides may be modified using ordinary molecular biological techniques to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

Pharmaceutical Compositions and Therapies

Administration of a SEMA 7A inhibitor comprising one or more peptides, small molecules, antisense nucleic acids, soluble receptors, or antibodies of the invention in a method of treatment can be achieved in a number of different ways, using methods known in the art. Such methods include, but are not limited to, providing exogenous peptide inhibitor, small molecule, soluble receptor, or an antibody to a subject or expressing a recombinant peptide inhibitor, small molecule, soluble receptor, or an antibody expression cassette.

In one embodiment, an exogenous SEMA 7A inhibitor peptide is administered to a subject. The exogenous peptide may also be a hybrid or fusion protein to facilitate, for instance, delivery to target cells or efficacy. In one embodiment, a hybrid protein may comprise a tissue-specific targeting sequence.

In another embodiment, an expression vector comprising an expression cassette encoding a SEMA 7A inhibitor protein, or fragment there of, or an antibody that will bind an epitope specific to SEMA 7A, a soluble SEMA 7A receptor, or a fragment thereof, is administered to a subject. An expression cassette may comprise a constitutive or inducible promoter. Such promoters are well known in the art, as are means for genetic modification. Expression vectors and methods for the introduction of exogenous DNA into cells with concomitant expression of the exogenous DNA in the cells are described, for example, in Sambrook et al. (2001, Molecular Cloning: A Laboratory Manual, Cold Spring Harbor Laboratory Press, Cold Spring Harbor, N.Y.), and in Ausubel et al.

(eds, 2005, Current Protocols in Molecular Biology, John Wiley & Sons, New York, N.Y.). In one embodiment, a cell comprising an expression vector of the invention is administered to a subject. Thus, the invention encompasses a cell comprising an isolated nucleic acid encoding a SEMA 7A inhibitory peptide, fusion protein or antibody of the invention.

Any expression vector compatible with the expression of a SEMA 7A inhibitory peptide, fusion protein, soluble receptor, or antibody of the invention is suitable for use in the instant invention, and can be selected from the group consisting of a plasmid DNA, a viral vector, and a mammalian vector. The expression vector, or a vector that is co-introduced with the expression vector, can further comprise a marker gene. Marker genes are useful, for instance, to monitor transfection efficiencies. Marker genes include: genes for selectable markers, including but not limited to, G418, hygromycin, and methotrexate, and genes for detectable markers, including, but not limited to, luciferase and GFP. The expression vector can further comprise an integration signal sequence which facilitates integration of the isolated polynucleotide into the genome of a target cell.

The therapeutic and prophylactic methods of the invention thus encompass the use of pharmaceutical compositions comprising a SEMA 7A inhibitory peptide, fusion protein, small molecule, soluble receptor, or antibody of the invention and/or an isolated nucleic acid encoding a SEMA 7A inhibitory peptide, fusion protein small molecule, soluble receptor, or antibody of the invention to practice the methods of the invention. The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 µM and 10 µM in a mammal.

Typically, dosages which may be administered in a method of the invention to an animal, preferably a human, range in amount from 0.5 µg is to about 50 mg per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 µg to about 10 mg per kilogram of body weight of the animal. More preferably, the dosage will vary from about 3 µg to about 1 mg per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the treatment of fibrosis include anti-inflammatories, including corticosteroids, and immunosuppressants.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Kits

The invention also includes a kit comprising a SEMA 7A inhibitor of the invention and an instructional material which describes, for instance, administering the SEMA 7A inhibitor to a subject as a prophylactic or therapeutic treatment or a non-treatment use as described elsewhere herein. In an embodiment, this kit further comprises a (preferably sterile) pharmaceutically acceptable carrier suitable for dissolving or suspending the therapeutic composition, comprising a SEMA 7A inhibitor, of the invention, for instance, prior to administering the molecule to a subject. Optionally, the kit comprises an applicator for administering the inhibitor. In one embodiment of the invention, the applicator is designed for pulmonary administration of the SEMA 7A inhibitor. In another embodiment, the kit comprises an antibody that specifically binds an epitope on SEMA 7A. Preferably, the antibody recognizes a human SEMA 7A.

A kit providing a nucleic acid encoding a peptide or antibody of the invention and an instructional material is also provided.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods used in the following experimental examples are now described.

Overexpression Transgenic and Null Mutant Mice

CC10-tTS-rtTA-TGF-$\beta_1$ Tg mice were generated, bred onto a C57BL/6 background for more than 10 generations, and used in these studies. These mice utilize the Clara cell 10-kDa protein (CC10) promoter to specifically target TGF-$\beta_1$ expression to the lung. The methods that were used to generate and characterize these mice were described previously (Lee et al., 2004, J Exp Med. 200:377-389).

Mice with null mutations of SEMA 7A that had been bred onto a C57BL/6 background for more than 10 generations were a generous gift from Dr Alex L. Kolodkin (Johns Hopkins University, Baltimore, Md. USA) (Pasterkamp et al., 2003a, supra; Pasterkamp et al., 2003b, supra). These mice were bred with the TGF-$\beta_1$ mice to obtain Tg mice with wild type (WT) and null SEMA7A loci. Genotyping of TGF-$\beta_1$ Tg and SEMA 7A null mice was accomplished according to the protocols previously established (Pasterkamp et al., 2003a, supra; Pasterkamp et al., 2003b, supra; Lee et al., 2004, supra).

Doxycycline (Dox) Water Administration

Six week old transgene (+) mice and transgene (−) littermate controls were randomized to normal water or water containing 0.5 mg/ml of dox as described previously (Lee et al., 2004, supra). Phenotypic alterations were evaluated at intervals thereafter.

Quantification of Lung Collagen

Animals were anesthetized, a median sternotomy was performed, and right heart perfusion was accomplished with calcium and magnesium-free phosphate-buffered saline (PBS). The heart and lungs were then removed en bloc. The right lung was frozen in liquid nitrogen and stored at −80° C. until used. Collagen content was determined by quantifying total soluble collagen using the Sircol Collagen Assay kit (Biocolor) according to the manufacturer's instructions. The data is expressed as the collagen content of the entire right lung.

Histologic Analysis

The lungs were removed en bloc as described above, inflated at 25 cm pressure with PBS containing 0.5% low melting point agarose gel, fixed, embedded in paraffin, sectioned and stained. Hematoxylin and eosin, and Mallory's trichrome stains were performed in the Research Histology Laboratory of the Department of Pathology at the Yale University School of Medicine.

Morphometric Analysis

Alveolar remodeling was estimated from the mean cord length of the airspace as described previously (Lee et al., 2004, supra; Zheng et al., 2000, J Clin Invest. 106:1081-1093).

Bronchoaveolar Lavage (BAL) and Lung Inflammation

Lung inflammation was assessed by BAL as described previously (Lee et al., 2004, supra). The BAL samples from each animal were pooled and centrifuged. The number and type of cells in the cell pellet were determined with light microscopy.

TdT-Mediated dUTP Nick-End Labeling (TUNEL) Evaluations

End labeling of exposed 3'-OH ends of DNA fragments was undertaken with the TUNEL in situ cell death detection kit AP (Roche Diagnostics) as described by the manufacturer. After staining, 20 fields of alveoli were randomly chosen for examination. The labeled cells were expressed as a percentage of total nuclei.

mRNA Analysis mRNA levels were assessed using real time, reverse transcription PCR assays as described by our laboratories (Lee et al., 2004, supra; Zheng et al., 2000, supra). In these assays, total cellular RNA from lungs were obtained using TRIZOL reagent (Invitrogen, Carlsbad, Calif.) according to the manufacturer's instructions. Primer sequences are found in Table 1. Primer sequences not in Table 1 have been previously reported.

TABLE 1

Real Time RT-PCR Primers

| Gene | Primer orientation | Primer sequence (5' to 3') | SEQ ID NO: |
|---|---|---|---|
| Sema7A | Forward | cctgaaagccatgttggtct | 3 |
|  | Reverse | tagcctttgagcgatgaggt | 4 |
| Plexin C1 | Forward | cagagacgccaatgacaaga | 5 |
|  | Reverse | tactgcactgctccatcagg | 6 |
| Integrin β1 | Forward | tggacaatgtcacctggaaa | 7 |
|  | Reverse | tgtgcccactgctgacttag | 8 |
| Egr-1 | Forward | gacgagttatcccagccaaa | 9 |
|  | Reverse | ggcagaggaagacgatgaag | 10 |
| TNF-a | Forward | cgtcagccgatttgctatct | 11 |
|  | Reverse | cggactccgcaaagtctaag | 12 |
| Bax | Forward | tgcagaggatgattgctgac | 13 |
|  | Reverse | ggaggaagtccagtgtccag | 14 |
| Col Iα1 | Forward | acgtcctggtgaagttggtc | 15 |
|  | Reverse | cagggaagcctctttctcct | 16 |
| Col Iα2 | Forward | ccgtgcttctcagaacatca | 17 |
|  | Reverse | gagcagccatcgactaggac | 18 |
| Lamin | Forward | aaacgaccctgttttcgttg | 19 |
|  | Reverse | caggttgaacacccctcagt | 20 |
| FGF2 | Forward | agcggctctactgcaagaac | 21 |
|  | Reverse | gccgtccatcttccttcata | 22 |
| CCN1 | Forward | gcacctcgagagaaggacac | 23 |
|  | Reverse | ggtcaagtggagaagggtga | 24 |
| CCN2 | Forward | caaagcagctgcaaatacca | 25 |
|  | Reverse | ggccaaatgtgtcttccagt | 26 |
| CCN3 | Forward | gcaccaagaaatccctgaaa | 27 |
|  | Reverse | gagggcagttggagtagcag | 28 |

TABLE 1-continued

Real Time RT-PCR Primers

| Gene | Primer orientation | Primer sequence (5' to 3') | SEQ ID NO: |
|---|---|---|---|
| CCN4 | Forward | cccctacaagtccaagacca | 29 |
| | Reverse | gagccacacacccacctaat | 30 |
| CCN5 | Forward | atacaggtgccaggaaggtg | 31 |
| | Reverse | gttggatactcgggtggcta | 32 |
| IL-18 | Forward | gcctcaaaccttccaaatca | 33 |
| | Reverse | gtgaagtcggccaaagttgt | 34 |

Quantification of TGF-$\beta_1$

The levels of BAL TGF-$\beta_1$ were determined by ELISA (R&D Systems, Inc., Minneapolis, Minn.) as per the manufacturer's instructions. These evaluations were done before and after acid activation to assess the levels of activated and total TGF-$\beta_1$ respectively.

Immunoblot Analysis

Lung lysates were prepared and Western analysis was undertaken with antibodies that reacted selectively with ICAD (Chemicon International, Temecula, Calif.), Smads 2 and 3 (Cell Signaling Technology, Danvers, Mass.) and phosphorylated Smads 2 and 3 (Cell Signaling Technology, Danvers, Mass.) as described previously (Lee et al., 2004, supra; Zheng et al., 2000, supra).

Bleomycin Administration

Bleomycin (0.075 Unit/mouse) or vehicle control were administered to C57BL/6 female mice as previously described by Jiang et al. (2004, J Clin Invest. 114:291-299).

Statistics

Normally distributed data are expressed as means±SEM and assessed for significance by Student's t test or ANOVA as appropriate. Data that were not normally distributed were assessed for significance using the Wilcoxon rank sum test.

The results of the experimental examples are now described.

Experimental Example 1

TGF-$\beta_1$ Regulation of the SEMA 7A System

To examine the possibility that SEMA 7A contributes to TGF-$\beta_1$-induced responses in the lung, studies were undertaken to determine if the expression of SEMA 7A or its putative receptors are regulated by transgenic TGF-$\beta_1$. This was done by comparing the levels of SEMA 7A, plexin C1 and $\beta_1$ integrins in lungs from transgene (Tg) negative (−) and Tg (+) mice at various times after Tg activation.

These studies demonstrate that TGF-$\beta_1$ is a potent stimulator of SEMA 7A, plexin C1 and $\beta_1$ integrin mRNA accumulation in lungs from dox-treated Tg mice (FIG. 1). This induction was seen after as little as 2 days of dox administration and persisted throughout the 28-day study interval (FIG. 1). Interestingly, the data also demonstrate that the induction of plexin C1 and $\beta_1$ integrins was SEMA 7A-dependent because TGF-$\beta_1$ did not induce either SEMA 7A receptor in SEMA 7A null mice (FIGS. 1B and 1C).

Thus, these studies demonstrate that TGF-$\beta_1$ is a potent stimulator of SEMA 7A and its receptors in the lung. They also demonstrate that SEMA 7A plays a critical role in the induction of its own receptors in this setting.

Experimental Example 2

Role of SEMA 7A in TFG-$\beta_1$-Induced Fibrosis

To determine if the fibrotic effects of TGF-$\beta_1$ are altered in the absence of SEMA 7A, biochemical (Sircol) and histologic approaches were used to quantitate the collagen in lungs from Tg mice with WT and null SEMA 7A loci.

Figure 2:
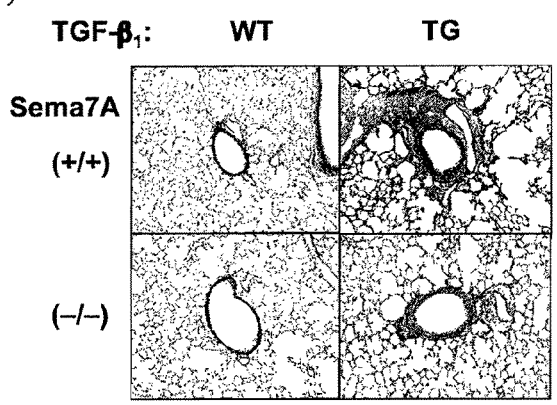
FIGS. 2A-2C are a series of images of lungs and bar graphs relating to studies of the roles of SEMA 7A in TGF-$\beta_1$-induced fibrosis and alveolar remodeling. Tg (−) (WT TGF-$\beta_1$) mice and Tg (+) (TG TGF-$\beta_1$ mice with wild type (+/+) and null (−/−) SEMA 7A loci were generated and evaluated after 2 weeks of transgene activation.
FIG. 2D depicts data from morphometric chord length assessments. The panels in FIGS. 2A and 2C are representative of at least 5 similar experiments. The values in FIGS. 2B and 2D represent the mean±SEM of evaluations in minimum of 5 mice (*p<0.002, **p<0.0001).
Figure 2:
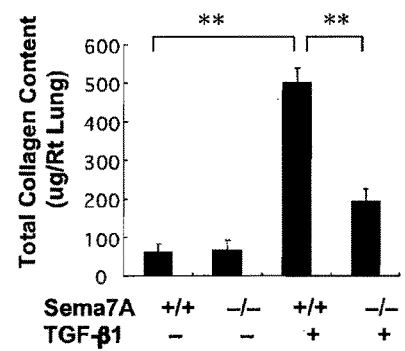
Figure 2:
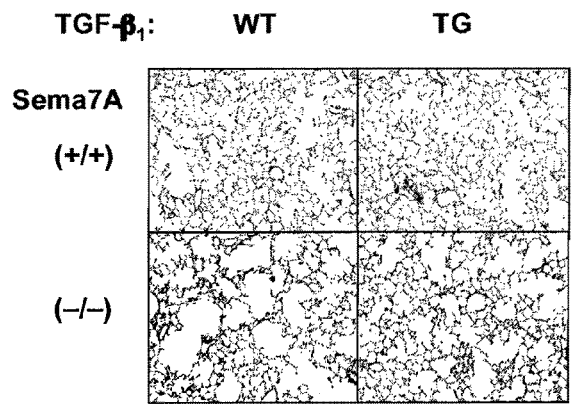
Figure 2:
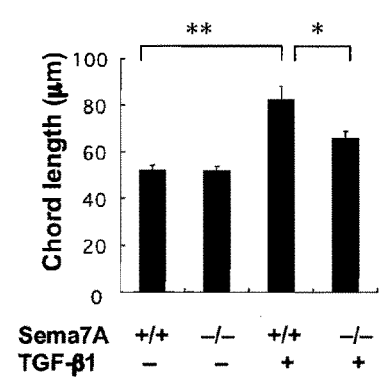

In accord with previous studies (Lee et al., 2004, supra), transgenic TGF-$\beta_1$ caused a significant increase in lung collagen content in mice that expressed SEMA 7A normally ($p<0.001$) (FIGS. 2A and B). Interestingly, this fibrotic response was diminished in the absence of SEMA 7A. After 14 days of dox water administration, TGF-$\beta_1$-induced collagen accumulation was decreased by 80.1+8.5% ($p<0.0001$) in SEMA 7A null versus WT animals (FIG. 2B).

These studies demonstrate that SEMA 7A plays an important role in the pathogenesis of TGF-$\beta_1$-induced pulmonary fibrosis in the lung.

Experimental Example 3

Role of SEMA 7A in Alveolar Remodeling

In addition to inducing tissue fibrosis, TGF-$\beta_1$ induces alveolar remodeling with septal destruction and an increase in alveolar cord length (Lee et al., 2004, supra). To define the role(s) of SEMA 7A in these responses, the alveoli of Tg mice with WT and null SEMA 7A loci were compared.

In accord with previous reports (Lee et al., 2004, supra), an increase in lung destruction was readily apparent in Tg mice that produced SEMA 7A normally (FIGS. 2C and 2D). Interestingly, null mutations of SEMA 7A caused a significant decrease in alveolar remodeling that was apparent in histologic and morphometric evaluations (FIGS. 2C and 2D). Overall, a null mutation of SEMA 7A caused a 72.3±8.6% decrease in the TGF-$\beta_1$-induced increase in alveolar chord length in mice on dox water for 2 weeks ($p<0.002$).

Thus, SEMA 7A plays an important role in the pathogenesis of TGF-$\beta_1$-induced alveolar remodeling in the lung.

Experimental Example 4

Role of SEMA 7A in TGF-$\beta_1$-Induced DNA Injury and Cell Death

Previous studies demonstrated that TGF-$\beta_1$ induces epithelial apoptosis and that this apoptotic response is a critical precursor of TGF-$\beta_1$-induced fibrosis (Lee et al., 2004, supra). Thus, studies were undertaken to test the hypothesis that SEMA 7A plays an important role in TGF-$\beta_1$-induced apoptosis. This was done using TUNEL stains to compare the TGF-$\beta_1$-induced DNA injury and cell death in transgenic mice with WT and null SEMA 7A loci.

Figure 3:
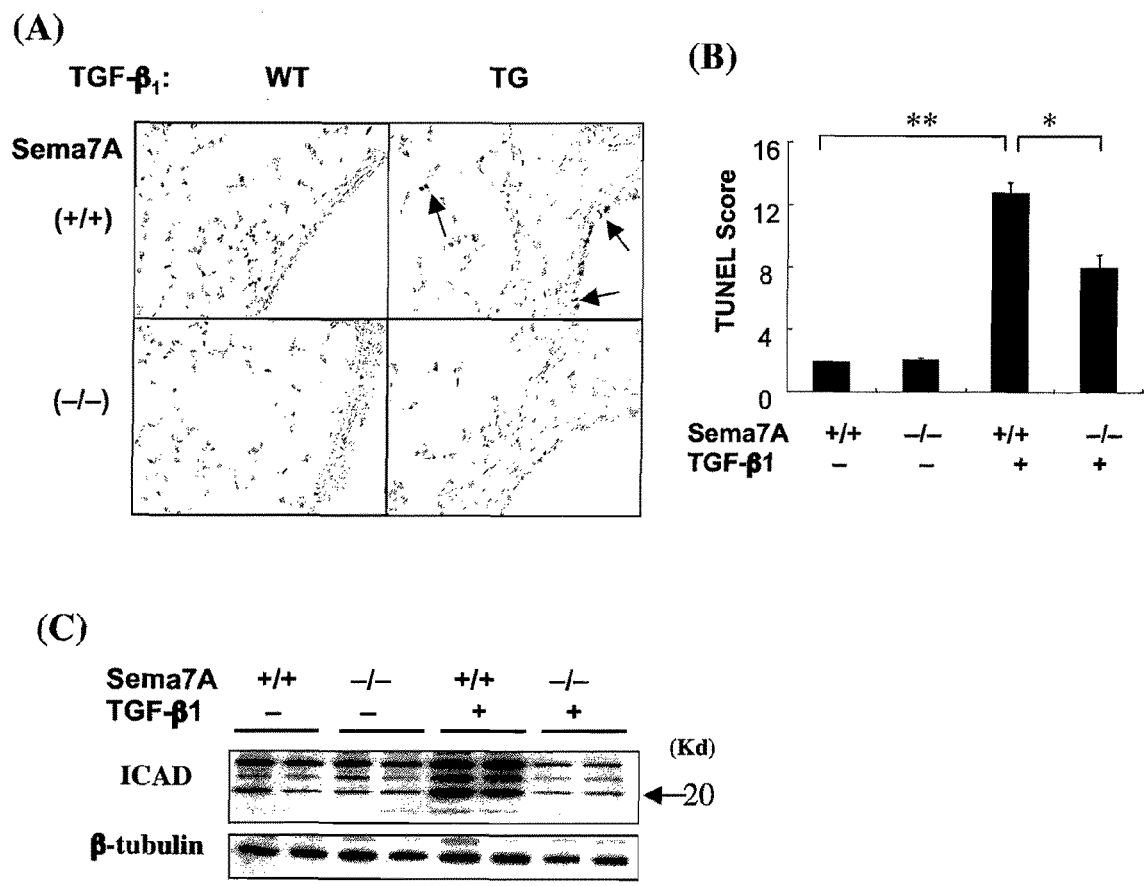
FIGS. 3A-3C are a series of images and a graph related to studies of the roles of SEMA 7A in TGF-$\beta_1$-induced DNA injury and cell death. Tg (−) (WT TGF-$\beta$1) mice and Tg (+) mice (TG TGF-$\beta_1$) with wild type (+/+) and null (−/−) SEMA 7A loci were generated and evaluated after 48 hour of transgene activation.

Transgenic TGF-$\beta_1$ caused an impressive increase in TUNEL staining in mice with WT SEMA 7A loci (FIGS. 3A and 3B). These TUNEL (+) cells were largely epithelial cells, as evidenced by their histologic location and morphology. This response was readily appreciated after 2 days of dox administration and decreased with longer periods of Tg activation (FIGS. 3A and 3B). At these time points, SEMA 7A appeared to play an important role in this response, because the TUNEL staining was decreased in lungs from Tg (+) mice with null mutations of SEMA 7A (FIGS. 3A and 3B). This was readily appreciated after 48 hours of dox administration where TGF-$\beta_1$-induced TUNEL staining was decreased by 43.3+/−3.5% compared to Tg mice with WT SEMA 7A loci (FIG. 3B) (p<0.011). This inhibition was associated with a significant decrease in caspase-mediated ICAD (inhibitor of caspase-activated DNase) cleavage (FIG. 3C).

Thus, these studies demonstrate that SEMA 7A is an important contributor to TGF-$\beta_1$-induced DNA injury and cell death in the lung.

Experimental Example 5

Role of SEMA 7A in TGF-$\beta_1$-Induced Inflammation

To determine if SEMA 7A contributed to TGF-$\beta_1$-induced tissue inflammation, the cellularity of BAL fluids and tissues from Tg (+) mice with wild type and null SEMA 7A loci were compared.

Similar numbers and types of cells were recovered in BAL fluids and tissues from Tg (−) mice regardless of their SEMA 7A genotype. In accord with prior studies (Lee et al., 2004, supra), transgenic TGF-$\beta_1$ augmented BAL and tissue cellularity by increasing macrophage and, to a lesser extent, lymphocyte and eosinophil accumulation. Importantly, the absence of SEMA 7A did not alter the magnitude or differential of these responses.

Thus, these studies demonstrate that SEMA 7A is not a major regulator of TGF-$\beta_1$-induced inflammation in the murine lung.

Experimental Example 6

SEMA 7A Regulation of Transgenic TGF-$\beta_1$ and Smads

The decreased ability of TGF-$\beta_1$ to induce tissue responses in the absence of SEMA 7A could be due to a decrease in the production of transgenic TGF-$\beta_1$ or a decrease in its ability to activate its effector pathways. To differentiate amongst these options, the levels of total and active TGF-$\beta_1$ in lungs from Tg (−) and Tg (+) mice with WT and null SEMA 7A loci were compared.

As can be seen in FIG. 4A, these effects appeared to be due, in great extent, to alteration(s) in TGF-$\beta_1$ effector pathway activation because the levels of total and bioactive TGF-$\beta_1$ in BAL from Tg (+) mice with null SEMA 7A loci were comparable or greater than those in fluids from Tg (+) mice that make SEMA 7A normally.

To address the mechanism by which SEMA 7A contributed to TGF-$\beta_1$ effector responses, is was determined if a deficiency of SEMA 7A altered the ability of TGF-$\beta_1$ to induce or activate Smads. These studies were done by comparing the Smads in Tg (+) mice with WT and null SEMA 7A loci. Because Smads 2 and 3 mediate, and Smad 7 inhibits, TGF-$\beta_1$ effector pathway activation (Leask et al., 2004, FASEB J. 18:816-827; Nakao et al., 1999, J Clin Invest. 104:5-11), all 3 were evaluated.

The levels and phosphorylation status of Smads 2 and 3 were similar in lungs from Tg (−) mice with WT and null SEMA 7A loci (FIG. 4B). In accord with reports in the literature (Leask et al., 2004, supra), Smad 2/3 phosphorylation was increased in TGF-$\beta_1$ Tg (+) mice on dox water (FIG. 4B). Interestingly, the levels of phosphorylation of Smads 2 and 3 were similar in mice with WT and null SEMA 7A loci (FIG. 4B).

Figure 4:
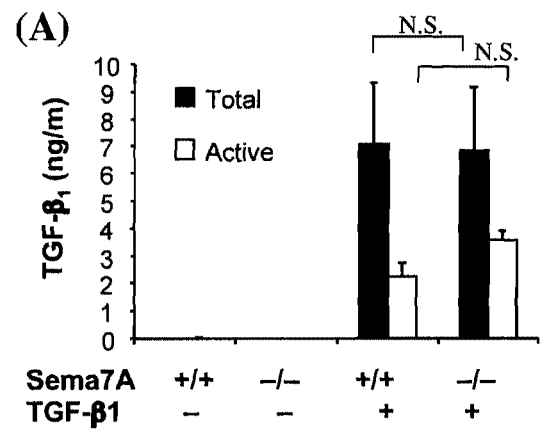
FIGS. 4A-4C are a series of graphs and images relating to studies of the roles of SEMA 7A in the regulation of TGF-$\beta_1$ and Smads. Tg (−) and Tg (+) mice with wild type (+/+) and null (−/−) SEMA 7A loci were generated and evaluated after 2 weeks of transgene activation.
Figure 4:
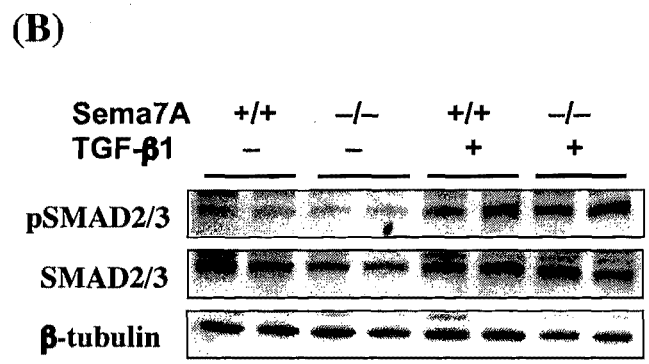
Figure 4:
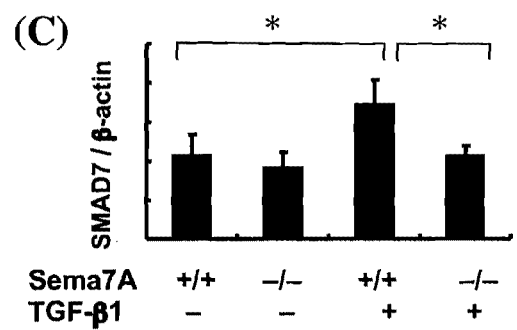

Transgenic TGF-$\beta_1$ also increased the levels of mRNA encoding of Smad 7 in mice with WT SEMA 7A loci (FIG. 4C). This induction, however, was significantly decreased in Tg (+) mice with null SEMA 7A loci (FIG. 4 C).

When viewed in combination, these studies demonstrate that the defect in TGF-31 effector activation noted in SEMA 7A null mice was not associated with a decrease in Smad 2/3 phosphorylation or an increase in the expression of Smad 7.

Experimental Example 7

SEMA 7A and TGF-$\beta_1$-Induced Apoptosis

Figure 5:
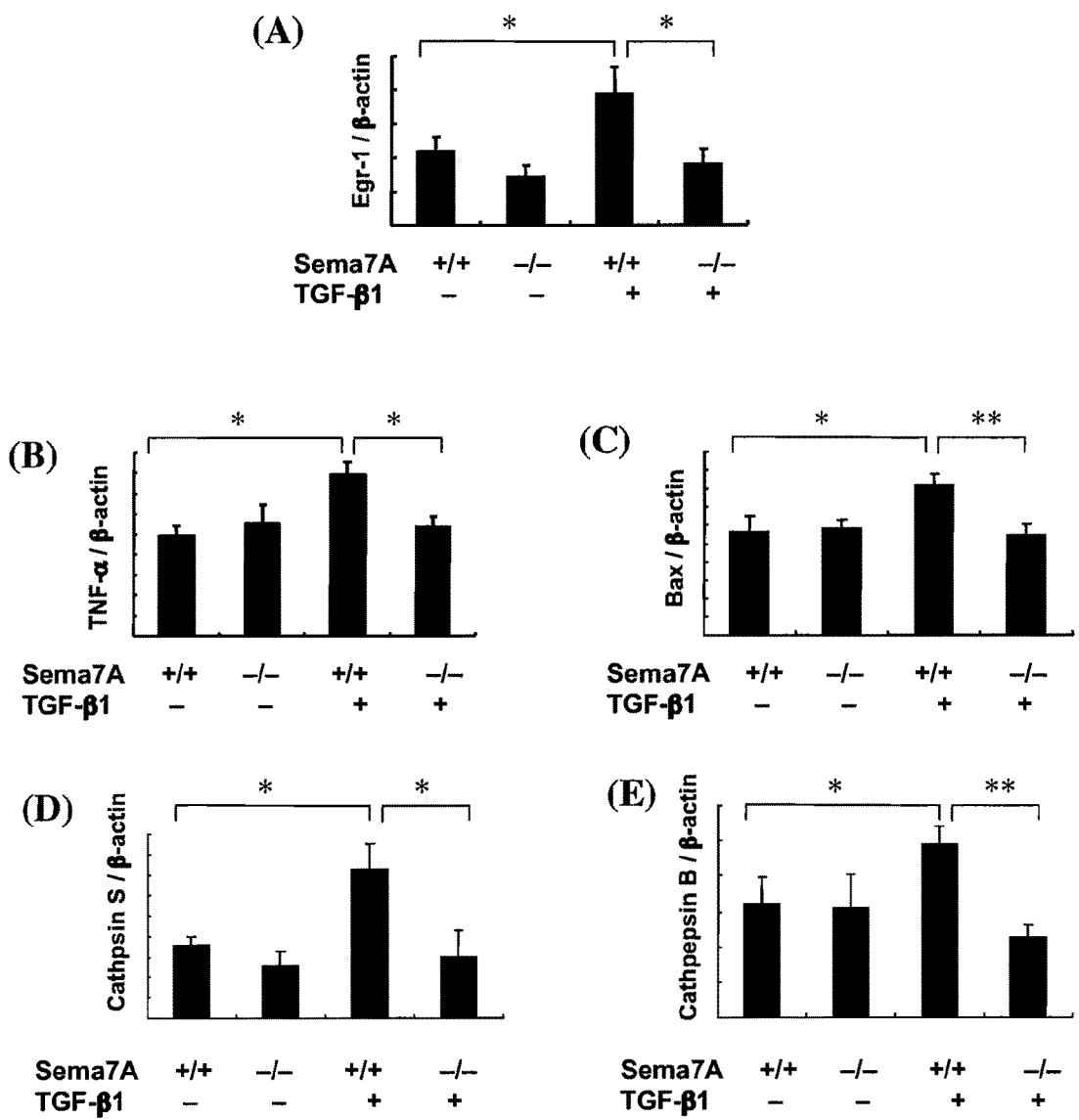
FIGS. 5A-5E are a series of graphs relating to the studies of the roles of SEMA 7A in the regulation of apoptosis regulators. Tg (−) and Tg (+) mice with wild type (+/+) and null (−/−) SEMA 7A loci were generated and evaluated after 2 weeks of transgene activation. Real time RT-PCR was used to quantitate and the levels of mRNA encoding: Egr-1 (FIG. 5A); TNF (FIG. 5B); Bax (FIG. 5C); cathepsin S FIG. 5D); and cathepsin B (FIG. 5E). The values represent the mean±SEM of evaluations in a minimum of 5 mice (*p<0.05, **p<0.01).
Figure 6:
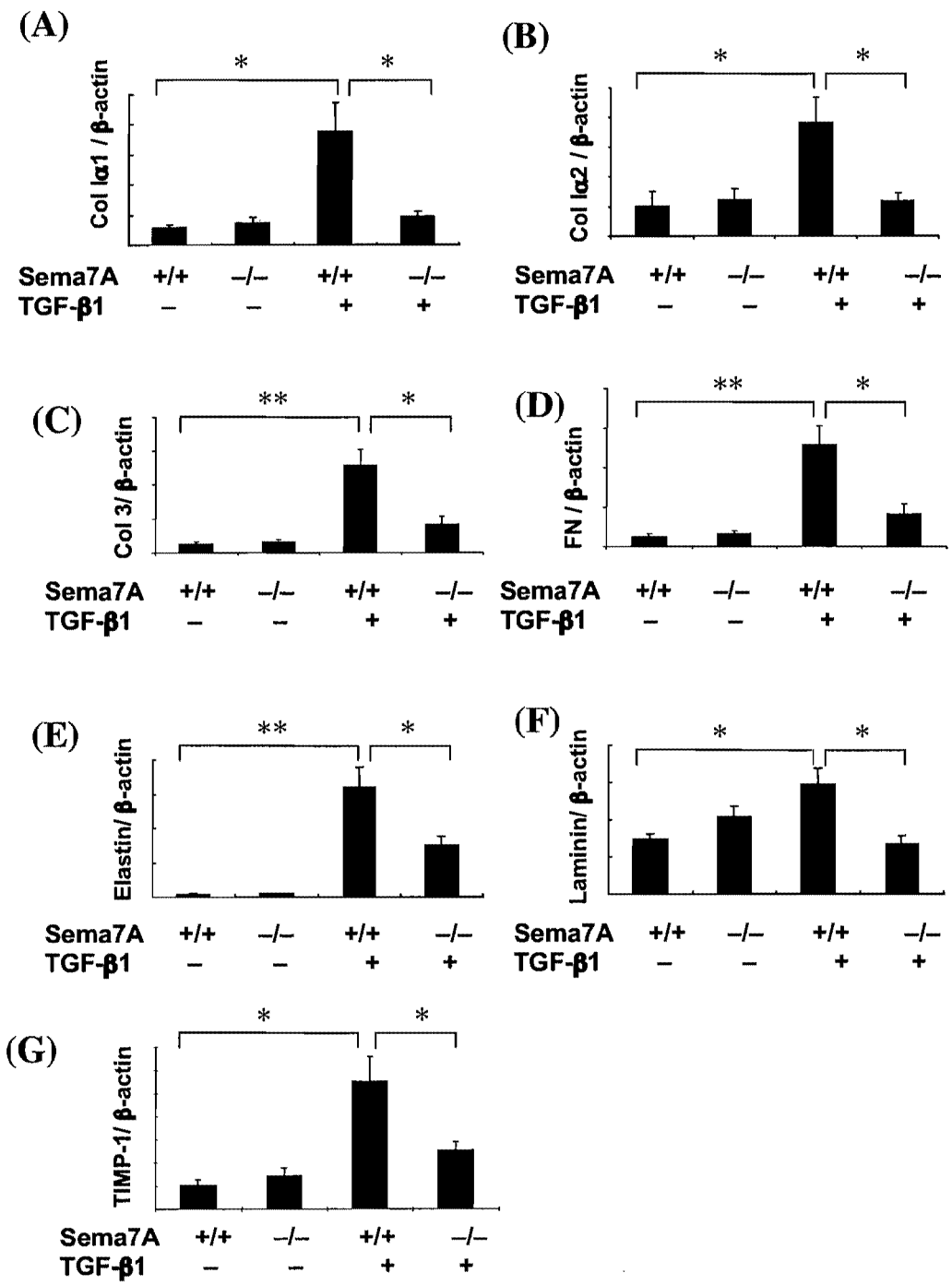
FIGS. 6A-6G are a series of graphs relating to the studies of the roles of SEMA 7A in the regulation of ECM proteins and anti-proteases. Tg (−) and Tg (+) mice with wild type (+/+) and null (−/−) SEMA 7A loci were generated and evaluated after 2 weeks of transgene activation. Real time RT-PCR was used to quantitate and the levels of mRNA encoding: α1(I) collagen (FIG. 6A; α1(II) collagen (FIG. 6B); type collagen (FIG. 6C); fibronectin (FN) (FIG. 6D); elastin (FIG. 6E); laminin (FIG. 6F); and TIMP-1 (FIG. 6G). The values represent the mean±SEM of evaluations in a minimum of 5 mice (*p<0.01, **p<0.001).

Previous studies from our laboratory demonstrated that TGF-$\beta_1$ induces lung epithelial cell apoptosis via an Egr-1-dependent mechanism that involves multiple cell death pathways (31). Thus, to address the mechanisms by which SEMA 7A might contribute to TGF-$\beta_1$-induced apoptosis, the ability of TGF-$\beta_1$ to regulate Egr-1, the mitochondrial cell death pathway activator Bax and death receptor cell death pathway activator TNF were evaluated. TGF-$\beta_1$ was a potent stimulator of the levels of mRNA encoding all 3 moieties (FIG. 5, A-C). Cathepsin-S and -B, which have also been implicated in lung epithelial cell apoptosis (32), were similarly stimulated (FIG. 5, D and E). These responses were mediated, at least in part, by SEMA 7A because null mutations of SEMA 7A decreased the ability of TGF-$\beta_1$ to stimulate Egr-1, Bax, TNF and the cathepsins (FIG. 5). When viewed in combination, these studies demonstrate that SEMA 7A plays an important role in TGF-$\beta_1$ stimulation of Egr-1 and the activation of the death receptor, mitochondrial and cathepsin-mediated cell death pathways.

Experimental Example 8

SEMA 7A and the Mechanisms of Pulmonary Fibrosis and Alveolar Remodeling

To address the mechanisms by which SEMA 7A might contribute to the pathogenesis of TGF-$\beta_1$-induced fibrosis and alveolar remodeling, the regulation of collagens and selected proteases and anti-proteases in lungs from TGF-$\beta_1$ Tg mice with WT and null SEMA 7A loci were characterized.

These studies demonstrated that TGF-$\beta_1$ is a potent stimulator of the accumulation of mRNA encoding $\alpha 1(I)$, $\alpha 1(II)$ and type III collagens, fibronectin (FN), elastin and laminin but not type IV collagen (FIGS. 6A-6F). Tg TGF-$\beta_1$ also stimulated the expression of mRNA encoding TIMP-1 (FIG. 6G). In all cases, SEMA 7A played an essential role in these inductive events because the ability of TGF-$\beta_1$ to regulate the accumulation of mRNA encoding these moieties was significantly decreased in mice with null mutations of SEMA 7A (FIG. 6).

Figure 7:
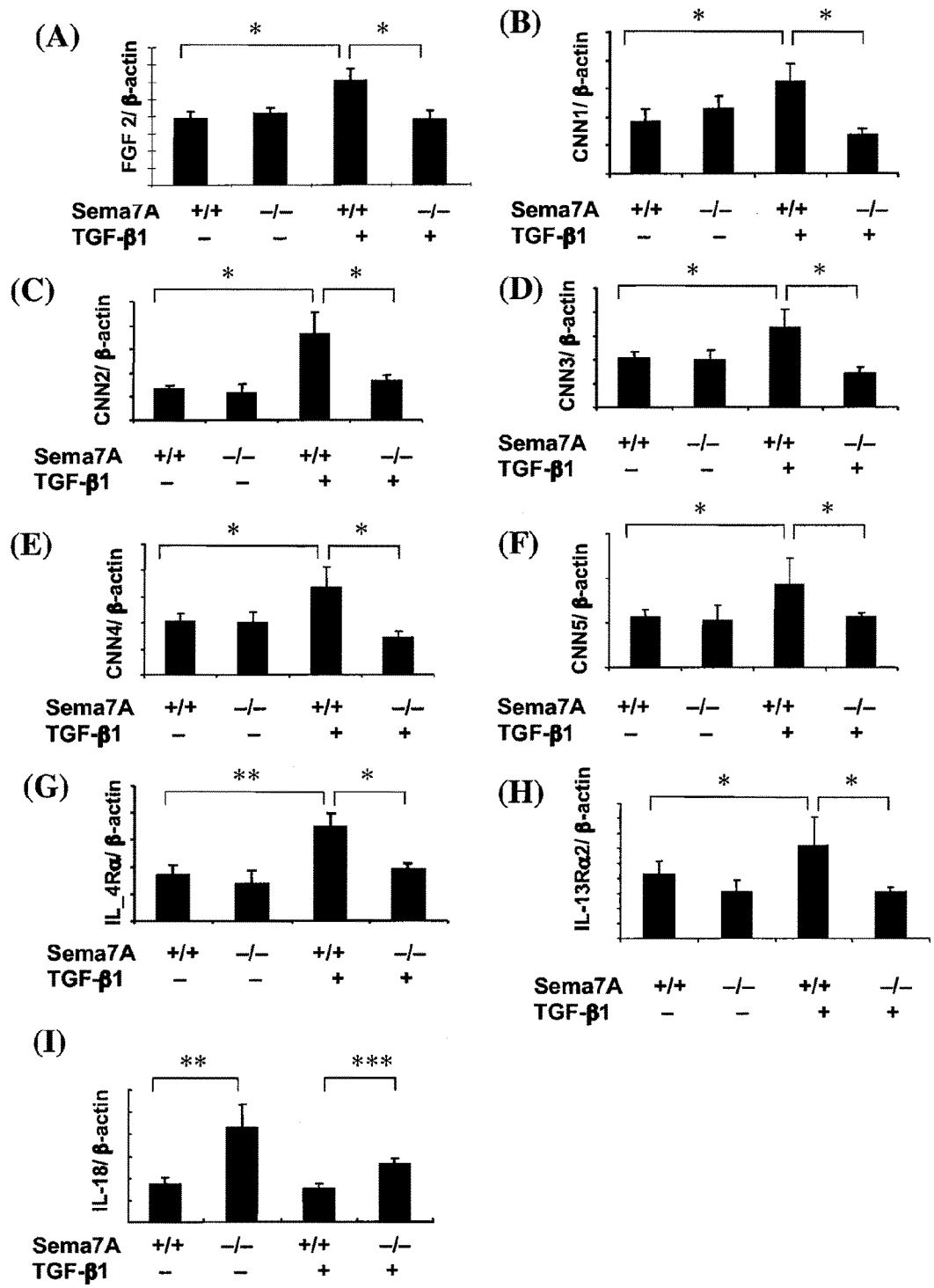
FIGS. 7A-7I are a series of graphs relating to the studies of the roles of SEMA 7A in the regulation of fibroregulatory cytokines and IL-13 receptor components. Tg (−) and Tg (+) mice with wild type (+/+) and null (−/−) SEMA 7A loci were generated and evaluated after 2 weeks of transgene activation. Real time RT-PCR was used to quantitate the levels of mRNA encoding: FGF2 (FIG. 7A); CCN1 (FIG. 7B); CCN2 (FIG. 7C); CCN3 (FIG. 7D); CCN4 (FIG. 7E); CCN5 (FIG. 7F); IL-4Rα (FIG. 7G); IL-13R2 (FIG. 7H); and IL-18 (FIG. 7I). The values represent the mean±SEM of evaluations in a minimum of 5 mice (*p<0.01, p<0.001, *p<0.039).

Studies were also undertaken to determine if the ability of TGF-$\beta_1$ to regulate other known fibroregulatory cytokines and their receptors was altered in the absence of SEMA 7A. Transgenic TGF-$\beta_1$ caused significant increases in the levels of mRNA encoding FGF 2 (FIG. 7A) the CCN growth factor family proteins; CCN1 (Cyr-61), CCN2 (connective tissue growth factor; CTGF), CCN3 (NOV), CCN4 (WISP-1) and CCN5 (WISP-2) (FIGS. 7B-7F) and the IL-13 and IL-4 receptor components IL-4R$\alpha$ and IL-13R$\alpha$2 (FIGS. 7G and 7H). In accord with the findings for the ECM proteins, these stimulatory effects were also SEMA-7A-dependent, since they were all ameliorated in Tg (+) mice with null SEMA 7A loci (FIGS. 7A-7H). In contrast, IL-18, which inhibits tissue fibrosis (Nakatani-Okuda et al., 2005, Am J Physiol Lung Cell Mol. Physiol. 289:L280-287), was inhibited by SEMA 7A in Tg (−) and Tg (+) mice (FIG. 7I).

These studies demonstrate that SEMA 7A plays a critical role in the ability of TGF-$\beta_1$ to augment the accumulation of mRNA encoding collagens and other ECM proteins, antiproteases, fibrostimulatory cytokines and IL-13 receptors, while inhibiting the expression of IL-18.

Experimental Example 9

SEMA 7A in Bleomycin-Induced Pulmonary Fibrosis

Studies were also undertaken to determine if the biology of SEMA 7A that was defined using the Tg modeling system was also relevant to fibrotic responses that were induced by other stimuli. Bleomycin was chosen because TGF-$\beta_1$ is known to play an important role in the pathogenesis of the fibrosis it induces (Daniels et al., 2004, J Clin Invest. 114: 1308-131618; Nakao et al., 1999, J Clin Invest. 104:5-11; Yehualaeshet et al., 2000, Am J Respir Cell Mol. Biol. 23:204-212).

Figure 8:
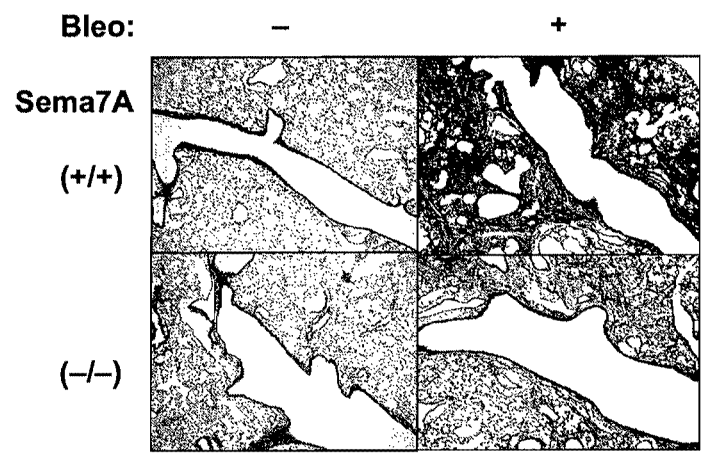
FIGS. 8A and 8B are an image and a graph related to studies of the role of SEMA 7A in bleomycin-induced fibrosis. Tg (−) and Tg (+) mice with wild type (+/+) and null (−/−) SEMA 7A loci were generated, given intratracheal bleomycin or its vehicle control and evaluated 3 weeks later.
Figure 8:
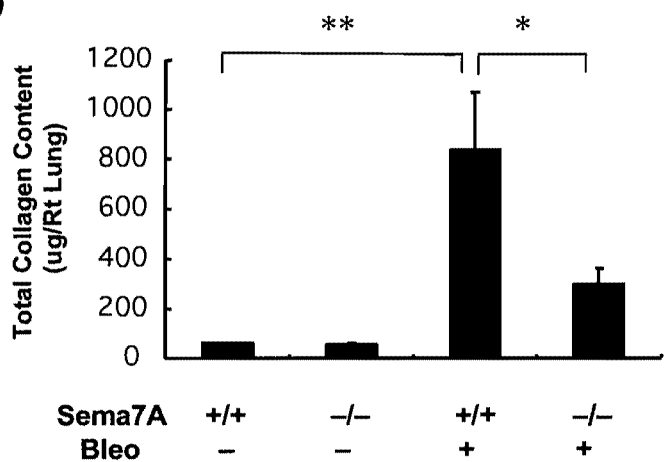

As seen in FIG. 8, bleomycin caused a significant increase in pulmonary fibrosis and collagen accumulation that was most impressive 3 weeks after intratracheal administration. In keeping with the results noted in the TGF-$\beta_1$ Tg mice, the fibrotic effects of bleomycin were significantly diminished in SEMA 7A null animals (FIGS. 8A and 8B). At the 3 week time point, SEMA 7A deficiency decreased bleomycin-induced pulmonary collagen accumulation by 90.3±7% (p<0.001).

Thus, SEMA 7A plays an important role in the pathogenesis of the fibrotic responses induced by bleomycin, as well as transgenic TGF-$\beta_1$.

Experimental Example 10

SEMA 7A in Bleomycin-Induced Pulmonary Fibrosis

To assess whether inhibition of SEMA 7A in vivo modulated collagen accumulation, pulmonary collage accumulation in Tg(−) and Tg(+) mice administered different antibodies was assessed.

As shown in Table 2, in contrast, there is a small but significant decrease in collagen content of Tg(+) mice administered anti-SEMA 7A antibody compared to those administered a control anti-IgG antibody.

TABLE 2

| Mouse | Antibody | Total collagen content (μg/right lung) |
|---|---|---|
| Tg(−) | Anti-IgG | 120 (n = 4) |
|  | Anti-SEMA 7A | 131 (n = 4) |
| Tg(+) | Anti-IgG | 337 (n = 4)* |
|  | Anti-SEMA 7A | 283 (n = 5)* |

*p = 0.02 for Tg(+) IgG versus Tg(+) SEMA 7A.

Thus, inhibition of SEMA 7A activity in TGF-$\beta_1$-induced fibrosis reduces collagen content in the lung. In view of the results in Experimental Example 9 demonstrating that SEMA 7A plays a role in fibrosis of non-TGF-$\beta_1$ origin, it is therefore believed that inhibiting the activity of SEMA 7A will be effective in inhibiting pulmonary fibrosis of any origin.

Experimental Example 11

Antifibrotic effects of SEMA 7A antibodies in vivo

To examine the in vivo role of SEMA 7A in TGF-$\beta$-induced fibrosis, total collagen content (TCC) of the lung was assessed after treatment with SEMA 7A neutralizing antibody. Eight-week old wild type (WT) and CC10-rtTA-tTS-TGF-$\beta$ transgenic (TGF-$\beta$ TG) mice were used for the evaluation. Anti human/mouse SEMA 7A monoclonal antibody (Catalogue number MAB2068, R&D Systems, Inc., Minneapolis, Minn. USA) and isotype control antibody (IgG$_{2b}$) (sc-3884) (Santa Cruz Biotech. Inc.) were intra-nasally (I.N.) administered to the mice in a dose of 25 μg/mouse/day for 10 days after starting one day before transgene induction.

Figure 9:
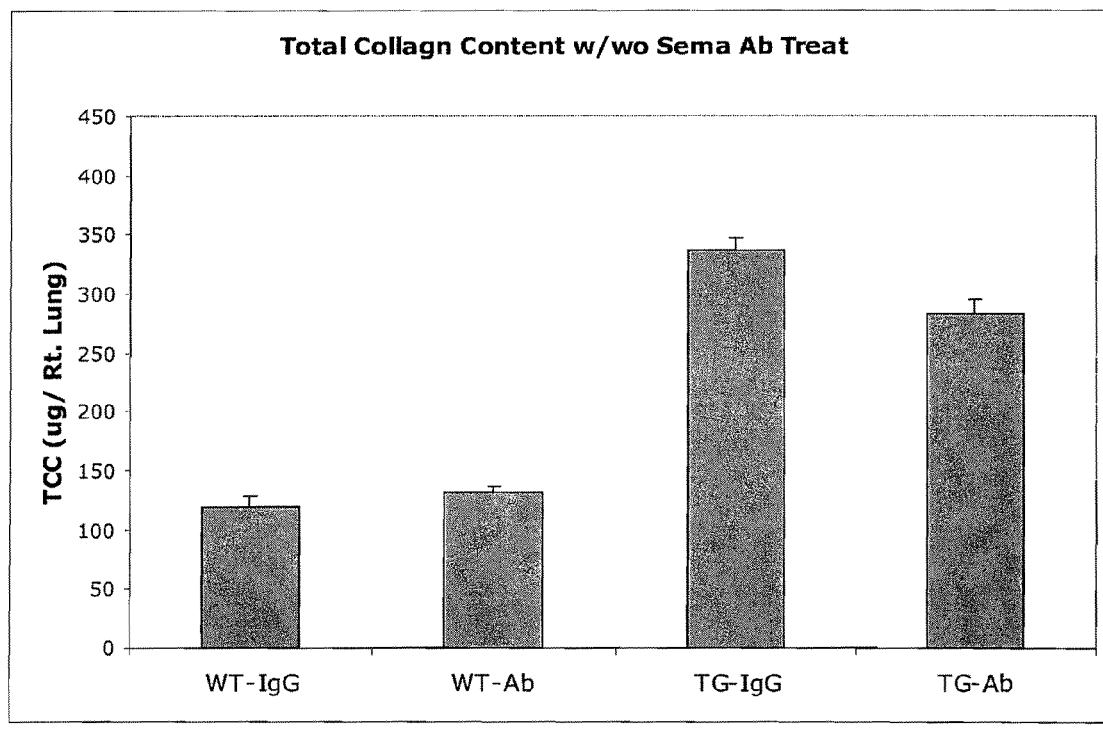
FIG. 9 is a graph depicting the antifibrotic effect of SEMA 7A neutralizing antibodies in vivo. TCC; total collagen content in the right lung. WT: wild type; WT-IgG: wild type mice treated with isotype antibody (IgG$_{2b}$); WT-Ab: wild type mice treated with sema 7A antibody; TG-IgG: TGF-$\beta$ transgenic mice treated with isotype antibody (IgG$_{2b}$); TG-Ab: TGF-$\beta$ transgenic mice treated with SEMA 7A antibody.

On day 11, the WT and TGF-$\beta$ TG mice were sacrificed and total collagen content of fight lung was evaluated by Sircol collagen assay as described previously (Lee et al., 2004, J. Exp. Med. 200:377-389). FIG. 9 and Table 3 show that total collagen content was significantly reduced in TGF-$\beta$ TG mice that were administered a SEMA 7A monoclonal antibody as compared to TGF-$\beta$ TG mice that were administered the isotype control antibody (IgG$_{2b}$).

TABLE 3

|  |  | Collagen (STD) |  | OD = 540 nM |  |
|---|---|---|---|---|---|
|  | S5 | 50 |  | 1.519 |  |
|  | S4 | 25 |  | 0.735 |  |
|  | S3 | 10 |  | 0.372 |  |
|  | S2 | 5 |  | 0.187 |  |
|  | S0 | 2.5 |  | 0.09 |  |
|  |  |  | Total | STDV | SEM |
| WC1 | 0.169 | 4.03853913 | 121.156174 |  |  |
| WC2 | 0.195 | 4.93282603 | 147.984781 |  |  |
| WC3 | 0.156 | 3.59139568 | 107.74187 |  |  |
| WC4 | 0.152 | 3.45381308 | 103.614392 | 120.124304 | 20.0264224 | 10.0132112 |
| WT1 | 0.189 | 4.72645213 | 141.793564 |  |  |
| WT2 | 0.187 | 4.65766083 | 139.729825 |  |  |
| WT3 | 0.177 | 4.31370433 | 129.41113 |  |  |
| WT4 | 0.163 | 3.83216523 | 114.964957 |  |  |
|  |  |  |  | 131.474869 | 12.439628 | 6.21981402 |
| TG380 | 0.369 | 10.9176692 | 327.530075 |  |  |
| TG387 | 0.402 | 12.0527256 | 361.581768 |  |  |
| TG389 | 0.353 | 10.3673388 | 311.020163 |  |  |
| TG390 | 0.39 | 11.6399778 | 349.1993340 | 337.332835 | 22.4890744 | 11.2445372 |

TABLE 3-continued

| | | | | | | |
|---|---|---|---|---|---|---|
| TG-AB-1 | 0.357 | 10.5049214 | 315.147641 | | | |
| TG-AB-2 | 0.325 | 9.40426055 | 282.127817 | | | |
| TG-AB-3 | 0.355 | 10.4361301 | 313.083902 | | | |
| TG-AB-5 | 0.305 | 8.71634755 | 261.490426 | | | |
| TG-AB-6 | 0.289 | 8.16601715 | 244.980514 | 283.36606 | 31.0110693 | 13.8685718 |
| | | | | p = | 0.02278394 | |

| | WT-IgG | WT-Ab | TG-IgG | TG-Ab |
|---|---|---|---|---|
| Average | 120.124304 | 131.474869 | 337.332835 | 283.36606 |
| SEM | 8.34434266 | 5.18317835 | 9.37044769 | 11.5571432 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting fibrosis in a mammal at risk of developing pulmonary fibrosis, said method comprising administering a therapeutically effective amount of a semaphorin 7A (SEMA 7A) inhibitor to said mammal, wherein said fibrosis is induced by TGF-β1 mediated collagen deposition, and wherein said SEMA 7A inhibitor is an anti-SEMA 7A antibody or SEMA 7A siRNA to inhibits TGF-β1 mediated collagen deposition thereby inhibiting the development of fibrosis in said mammal.

2. The method of claim 1, wherein said antibody is an antibody selected from a group consisting of a polyclonal antibody, a monoclonal antibody, a humanized antibody, a human antibody, and an antigen-binding fragment of an antibody, wherein the antigen-binding fragment is a Fab fragment, a F(ab')2 fragment, or combination thereof.

3. The method of claim 1, wherein said mammal is a human.

4. A method of inhibiting fibrosis in a mammal diagnosed with pulmonary fibrosis, said method comprising administering a therapeutically effective amount of a SEMA 7A inhibitor to said mammal, wherein said fibrosis is induced by TGF-β1 mediated collagen deposition, and wherein said SEMA 7A inhibitor is an anti-SEMA 7A antibody or SEMA 7A siRNA to inhibits TGF-β1 mediated collagen deposition thereby inhibiting fibrosis in said mammal.

5. The method of claim 4, wherein said antibody is an antibody selected from a group consisting of a polyclonal antibody, a monoclonal antibody, a humanized antibody, a human antibody, and an antigen-binding fragment of an antibody, wherein the antigen-binding fragment is a Fab fragment, a F(ab')2 fragment, or combinations thereof.

6. The method of claim 4, wherein said mammal is a human.

7. A method of inhibiting alveolar remodeling in a mammal diagnosed with pulmonary fibrosis, said method comprising administering a therapeutically effective amount of a SEMA 7A inhibitor to said mammal, wherein said fibrosis is induced by TGF-β1-mediated collagen deposition, and wherein said SEMA 7A inhibitor is an anti-SEMA 7A antibody or SEMA 7A siRNA that inhibits TGF-β1 mediated collagen deposition thereby inhibiting alveolar remodeling and fibrosis in said mammal.

8. The method of claim 7, wherein said antibody is an antibody selected from a group consisting of a polyclonal antibody, a monoclonal antibody, a humanized antibody, a human antibody, and an antigen-binding fragment of an antibody, wherein the antigen-binding fragment is a Fab fragment, a F(ab')2 fragment, or combinations thereof.

9. The method of claim 7, wherein said mammal is human.

10. A method of inhibiting lung epithelial cell apoptosis in a mammal diagnosed with pulmonary fibrosis, said method comprising administering a therapeutically effective amount of a SEMA 7A inhibitor to said mammal, wherein said fibrosis is induced by TGF-β1 mediated collagen deposition, and wherein said SEMA 7A inhibitor is an anti-SEMA 7A antibody or SEMA 7A siRNA that inhibits TGF-β1 mediated collagen deposition thereby inhibiting lung epithelial cell apoptosis in said mammal.

11. The method of claim 10, wherein said antibody is an antibody selected from a group consisting of a polyclonal antibody, a monoclonal antibody, a humanized antibody, a human antibody, and an antigen-binding fragment of an antibody, wherein the antigen-binding fragment is a Fab fragment, a F(ab')2 fragment, or combinations thereof.

12. The method of claim 10, wherein said mammal is human.

13. A method of inhibiting TGF-β1 mediated pathological collagen deposition in lung of a mammal with pulmonary fibrosis, said method comprising administering a therapeutically effective amount of a SEMA 7A inhibitor to said mammal, and wherein said SEMA 7A inhibitor is an anti-SEMA 7A antibody or SEMA 7A siRNA that inhibits TGF-β1 mediated pathological collagen deposition in lung of said mammal.

14. The method of claim 13, wherein said antibody is an antibody selected from a group consisting of a polyclonal antibody, a monoclonal antibody, a humanized antibody, a human antibody, and an antigen-binding fragment of an antibody, wherein the antigen-binding fragment is a Fab fragment, a F(ab')2 fragment, or combinations thereof.

15. The method of claim 13, wherein said mammal is human.

* * * * *

SEQUENCE LISTING

<160> NUMBER OF SEQ ID NOS: 34

<210> SEQ ID NO 1
<211> LENGTH: 2636
<212> TYPE: DNA
<213> ORGANISM: Homo sapiens

<400> SEQUENCE: 1

```
cggggccacg ggatgacgcc tcctccgccc ggacgtgccg ccccagcgc accgcgcgcc      60
cgcgtccctg gcccgccggc tcggttgggg cttccgctgc ggctgcggct gctgctgctg     120
ctctgggcgg ccgccgcctc cgcccagggc cacctaagga gcggacccg catcttcgcc     180
gtctggaaag gccatgtagg gcaggaccgg gtggactttg ccagactga gccgcacacg      240
gtgcttttcc acgagccagg cagctcctct gtgtgggtgg gaggacgtgg caaggtctac     300
ctctttgact tccccgaggg caagaacgca tctgtgcgca cggtgaatat cggctccaca     360
aaggggtcct gtctggataa gcgggactgc gagaactaca tcactctcct ggagaggcgg     420
agtgaggggc tgctggcctg tggcaccaac gcccggcacc ccagctgctg gaacctggtg     480
aatggcactg tggtgccact tggcgagatg agaggctacg cccccttcag cccggacgag     540
aactccctgg ttctgtttga aggggacgag gtgtattcca ccatccggaa gcaggaatac     600
aatgggaaga tccctcggtt ccgccgcatc cggggcgaga gtgagctgta caccagtgat     660
actgtcatgc agaacccaca gttcatcaaa gccaccatcg tgcaccaaga ccaggcttac     720
gatgacaaga tctactactt cttccgagag gacaatcctg acaagaatcc tgaggctcct     780
ctcaatgtgt cccgtgtggc ccagttgtgc agggggggacc agggtgggga aagttcactg     840
tcagtctcca agtggaacac ttttctgaaa gccatgctgg tatgcagtga tgctgccacc     900
aacaagaact tcaacaggct gcaagacgtc ttcctgctcc ctgacccag cggccagtgg     960
agggacacca gggtctatgg tgttttctcc aacccctgga actactcagc cgtctgtgtg    1020
tattccctcg gtgacattga caaggtcttc cgtacctcct cactcaaggg ctaccactca    1080
agccttccca acccgcggcc tggcaagtgc ctcccagacc agcagccgat acccacagag    1140
accttccagg tggctgaccg tcacccgagt gtggcgcaga gggtggagcc catgggcct     1200
ctgaagacgc cattgttcca ctctaaatac cactaccaga aagtggccgt tcaccgcatg    1260
caagccagcc acggggagac ctttcatgtg ctttacctaa ctacagacag gggcactatc    1320
cacaaggtgg tggaaccggg ggagcaggag cacagcttcg ccttcaacat catggagatc    1380
```

-continued

```
cagcccttcc gccgcgcggc tgccatccag accatgtcgc tggatgctga gcggaggaag    1440
ctgtatgtga gctcccagtg ggaggtgagc caggtgcccc tggacctgtg tgaggtctat    1500
ggcgggggct gccacggttg cctcatgtcc cgagacccct actgcggctg ggaccagggc    1560
cgctgcatct ccatctacag ctccgaacgg tcagtgctgc aatccattaa tccagccgag    1620
ccacacaagg agtgtcccaa ccccaaacca gacaaggccc cactgcagaa ggtttccctg    1680
gccccaaact ctcgctacta cctgagctgc cccatggaat cccgccacgc cacctactca    1740
tggcgccaca aggagaacgt ggagcagagc tgcgaacctg gtcaccagag ccccaactgc    1800
atcctgttca tcgagaacct cacggcgcag cagtacggcc actacttctg cgaggcccag    1860
gagggctcct acttccgcga ggctcagcac tggcagctgc tgcccgagga cggcatcatg    1920
gccgagcacc tgctgggtca tgcctgtgcc ctggctgcct ccctctggct gggggtgctg    1980
cccacactca ctcttggctt gctggtccac tagggcctcc cgaggctggg catgcctcag    2040
gcttctgcag cccagggcac tagaacgtct cacactcaga gccggctggc ccgggagctc    2100
cttgcctgcc acttcttcca ggggacagaa taacccagtg aggatgcca ggcctggaga     2160 cgtccagccg caggcggctg ctgggccccca ggtggcgcac ggatggtgag gggctgagaa   2220
tgagggcacc gactgtgaag ctggggcatc gatgacccaa gactttatct tctggaaaat    2280
atttttcaga ctcctcaaac ttgactaaat gcagcgatgc tcccagccca agagcccatg    2340
ggtcggggag tgggtttgga taggagagct gggactccat ctcgaccctg gggctgaggc    2400
ctgagtcctt ctggactctt ggtacccaca ttgcctcctt cccctccctc tctcatggct    2460
gggtggctgg tgttcctgaa acccagggc taccctctgt ccagccctgt cctctgcagc     2520
tccctctctg gtcctgggtc ccacaggaca gccgccttgc atgtttattg aaggatgttt    2580
gctttccgga cggaaggacg gaaaaagctc tgaaaaaaaa aaaaaaaaaa aaaaaa        2636
```

<210> SEQ ID NO 2
<211> LENGTH: 666
<212> TYPE: PRT
<213> ORGANISM: Homo sapiens

<400> SEQUENCE: 2

```
Met Thr Pro Pro Pro Gly Arg Ala Ala Ser Ala Pro Arg Ala
1               5                   10                  15

Arg Val Pro Gly Pro Pro Ala Arg Leu Gly Leu Pro Leu Arg Leu Arg
                20                  25                  30

Leu Leu Leu Leu Leu Trp Ala Ala Ala Ser Ala Gln Gly His Leu
            35                  40                  45

Arg Ser Gly Pro Arg Ile Phe Ala Val Trp Lys Gly His Val Gly Gln
        50                  55                  60

Asp Arg Val Asp Phe Gly Gln Thr Glu Pro His Thr Val Leu Phe His
65                  70                  75                  80

Glu Pro Gly Ser Ser Ser Val Trp Val Gly Arg Gly Lys Val Tyr
                85                  90                  95

Leu Phe Asp Phe Pro Glu Gly Lys Asn Ala Ser Val Arg Thr Val Asn
                100                 105                 110

Ile Gly Ser Thr Lys Gly Ser Cys Leu Asp Lys Arg Asp Cys Glu Asn
            115                 120                 125

Tyr Ile Thr Leu Leu Glu Arg Arg Ser Glu Gly Leu Leu Ala Cys Gly
        130                 135                 140

Thr Asn Ala Arg His Pro Ser Cys Trp Asn Leu Val Asn Gly Thr Val
145                 150                 155                 160
```

-continued

Val Pro Leu Gly Glu Met Arg Gly Tyr Ala Pro Phe Ser Pro Asp Glu
                165                 170                 175

Asn Ser Leu Val Leu Phe Glu Gly Asp Glu Val Tyr Ser Thr Ile Arg
                180                 185                 190

Lys Gln Glu Tyr Asn Gly Lys Ile Pro Arg Phe Arg Ile Arg Gly
                195                 200                 205

Glu Ser Glu Leu Tyr Thr Ser Asp Thr Val Met Gln Asn Pro Gln Phe
    210                 215                 220

Ile Lys Ala Thr Ile Val His Gln Asp Gln Ala Tyr Asp Asp Lys Ile
225                 230                 235                 240

Tyr Tyr Phe Phe Arg Glu Asp Asn Pro Asp Lys Asn Pro Glu Ala Pro
                245                 250                 255

Leu Asn Val Ser Arg Val Ala Gln Leu Cys Arg Gly Asp Gln Gly Gly
                260                 265                 270

Glu Ser Ser Leu Ser Val Ser Lys Trp Asn Thr Phe Leu Lys Ala Met
    275                 280                 285

Leu Val Cys Ser Asp Ala Ala Thr Asn Lys Asn Phe Asn Arg Leu Gln
290                 295                 300

Asp Val Phe Leu Leu Pro Asp Pro Ser Gly Gln Trp Arg Asp Thr Arg
305                 310                 315                 320

Val Tyr Gly Val Phe Ser Asn Pro Trp Asn Tyr Ser Ala Val Cys Val
                325                 330                 335

Tyr Ser Leu Gly Asp Ile Asp Lys Val Phe Arg Thr Ser Ser Leu Lys
                340                 345                 350

Gly Tyr His Ser Ser Leu Pro Asn Pro Arg Pro Gly Lys Cys Leu Pro
                355                 360                 365

Asp Gln Gln Pro Ile Pro Thr Glu Thr Phe Gln Val Ala Asp Arg His
                370                 375                 380

Pro Glu Val Ala Gln Arg Val Glu Pro Met Gly Pro Leu Lys Thr Pro
385                 390                 395                 400

Leu Phe His Ser Lys Tyr His Tyr Gln Lys Val Ala Val His Arg Met
                405                 410                 415

Gln Ala Ser His Gly Glu Thr Phe His Val Leu Tyr Leu Thr Thr Asp
                420                 425                 430

Arg Gly Thr Ile His Lys Val Val Glu Pro Gly Glu Gln Glu His Ser
                435                 440                 445

Phe Ala Phe Asn Ile Met Glu Ile Gln Pro Phe Arg Arg Ala Ala Ala
                450                 455                 460

Ile Gln Thr Met Ser Leu Asp Ala Glu Arg Arg Lys Leu Tyr Val Ser
465                 470                 475                 480

Ser Gln Trp Glu Val Ser Gln Val Pro Leu Asp Leu Cys Glu Val Tyr
                485                 490                 495

Gly Gly Gly Cys His Gly Cys Leu Met Ser Arg Asp Pro Tyr Cys Gly
                500                 505                 510

Trp Asp Gln Gly Arg Cys Ile Ser Ile Tyr Ser Ser Glu Arg Ser Val
                515                 520                 525

Leu Gln Ser Ile Asn Pro Ala Glu Pro His Lys Glu Cys Pro Asn Pro
                530                 535                 540

Lys Pro Asp Lys Ala Pro Leu Gln Lys Val Ser Leu Ala Pro Asn Ser
545                 550                 555                 560

Arg Tyr Tyr Leu Ser Cys Pro Met Glu Ser Arg His Ala Thr Tyr Ser
                565                 570                 575

Trp Arg His Lys Glu Asn Val Glu Gln Ser Cys Glu Pro Gly His Gln

|     |     |     |     |     | 580 |     |     |     | 585 |     |     |     |     | 590 |     |     |
| --- | --- | --- | --- | --- | --- | --- | --- | --- | --- | --- | --- | --- | --- | --- | --- | --- |

Ser Pro Asn Cys Ile Leu Phe Ile Glu Asn Leu Thr Ala Gln Gln Tyr
         595                 600                 605

Gly His Tyr Phe Cys Glu Ala Gln Gly Ser Tyr Phe Arg Glu Ala
    610                 615                 620

Gln His Trp Gln Leu Leu Pro Glu Asp Gly Ile Met Ala Glu His Leu
625                 630                 635                 640

Leu Gly His Ala Cys Ala Leu Ala Ala Ser Leu Trp Leu Gly Val Leu
                645                 650                 655

Pro Thr Leu Thr Leu Gly Leu Leu Val His
        660                 665

<210> SEQ ID NO 3
<211> LENGTH: 20
<212> TYPE: DNA
<213> ORGANISM: Artificial
<220> FEATURE:
<223> OTHER INFORMATION: Chemically synthesized

<400> SEQUENCE: 3
cctgaaagcc atgttggtct                                              20

<210> SEQ ID NO 4
<211> LENGTH: 20
<212> TYPE: DNA
<213> ORGANISM: Artificial
<220> FEATURE:
<223> OTHER INFORMATION: Chemically synthesized

<400> SEQUENCE: 4
tagcctttga gcgatgaggt                                              20

<210> SEQ ID NO 5
<211> LENGTH: 20
<212> TYPE: DNA
<213> ORGANISM: Artificial
<220> FEATURE:
<223> OTHER INFORMATION: Chemically synthesized

<400> SEQUENCE: 5
cagagacgcc aatgacaaga                                              20

<210> SEQ ID NO 6
<211> LENGTH: 20
<212> TYPE: DNA
<213> ORGANISM: Artificial
<220> FEATURE:
<223> OTHER INFORMATION: Chemically synthesized

<400> SEQUENCE: 6
tactgcactg ctccatcagg                                              20

<210> SEQ ID NO 7
<211> LENGTH: 20
<212> TYPE: DNA
<213> ORGANISM: Artificial
<220> FEATURE:
<223> OTHER INFORMATION: Chemically synthesized

<400> SEQUENCE: 7
tggacaatgt cacctggaaa                                              20

<210> SEQ ID NO 8
<211> LENGTH: 20

-continued

```
<212> TYPE: DNA
<213> ORGANISM: Artificial
<220> FEATURE:
<223> OTHER INFORMATION: Chemically synthesized

<400> SEQUENCE: 8
tgtgcccact gctgacttag                                              20

<210> SEQ ID NO 9
<211> LENGTH: 20
<212> TYPE: DNA
<213> ORGANISM: Artificial
<220> FEATURE:
<223> OTHER INFORMATION: Chemically synthesized

<400> SEQUENCE: 9
gacgagttat cccagccaaa                                              20

<210> SEQ ID NO 10
<211> LENGTH: 20
<212> TYPE: DNA
<213> ORGANISM: Artificial
<220> FEATURE:
<223> OTHER INFORMATION: Chemically synthesized

<400> SEQUENCE: 10
ggcagaggaa gacgatgaag                                              20

<210> SEQ ID NO 11
<211> LENGTH: 20
<212> TYPE: DNA
<213> ORGANISM: Artificial
<220> FEATURE:
<223> OTHER INFORMATION: Chemically synthesized

<400> SEQUENCE: 11
cgtcagccga tttgctatct                                              20

<210> SEQ ID NO 12
<211> LENGTH: 20
<212> TYPE: DNA
<213> ORGANISM: Artificial
<220> FEATURE:
<223> OTHER INFORMATION: Chemically synthesized

<400> SEQUENCE: 12
cggactccgc aaagtctaag                                              20

<210> SEQ ID NO 13
<211> LENGTH: 20
<212> TYPE: DNA
<213> ORGANISM: Artificial
<220> FEATURE:
<223> OTHER INFORMATION: Chemically synthesized

<400> SEQUENCE: 13
tgcagaggat gattgctgac                                              20

<210> SEQ ID NO 14
<211> LENGTH: 20
<212> TYPE: DNA
<213> ORGANISM: Artificial
<220> FEATURE:
<223> OTHER INFORMATION: Chemically synthesized

<400> SEQUENCE: 14
ggaggaagtc cagtgtccag                                              20
```

```
<210> SEQ ID NO 15
<211> LENGTH: 20
<212> TYPE: DNA
<213> ORGANISM: Artificial
<220> FEATURE:
<223> OTHER INFORMATION: Chemically synthesized

<400> SEQUENCE: 15
acgtcctggt gaagttggtc                                               20

<210> SEQ ID NO 16
<211> LENGTH: 20
<212> TYPE: DNA
<213> ORGANISM: Artificial
<220> FEATURE:
<223> OTHER INFORMATION: Chemically synthesized

<400> SEQUENCE: 16
cagggaagcc tctttctcct                                               20

<210> SEQ ID NO 17
<211> LENGTH: 20
<212> TYPE: DNA
<213> ORGANISM: Artificial
<220> FEATURE:
<223> OTHER INFORMATION: Chemically synthesized

<400> SEQUENCE: 17
ccgtgcttct cagaacatca                                               20

<210> SEQ ID NO 18
<211> LENGTH: 20
<212> TYPE: DNA
<213> ORGANISM: Artificial
<220> FEATURE:
<223> OTHER INFORMATION: Chemically synthesized

<400> SEQUENCE: 18
gagcagccat cgactaggac                                               20

<210> SEQ ID NO 19
<211> LENGTH: 20
<212> TYPE: DNA
<213> ORGANISM: Artificial
<220> FEATURE:
<223> OTHER INFORMATION: Chemically synthesized

<400> SEQUENCE: 19
aaacgaccct gttttcgttg                                               20

<210> SEQ ID NO 20
<211> LENGTH: 20
<212> TYPE: DNA
<213> ORGANISM: Artificial
<220> FEATURE:
<223> OTHER INFORMATION: Chemically synthesized

<400> SEQUENCE: 20
caggttgaac acccctcagt                                               20

<210> SEQ ID NO 21
<211> LENGTH: 20
<212> TYPE: DNA
<213> ORGANISM: Artificial
<220> FEATURE:
<223> OTHER INFORMATION: Chemically synthesized
```

<400> SEQUENCE: 21
agcggctcta ctgcaagaac                                                    20

<210> SEQ ID NO 22
<211> LENGTH: 20
<212> TYPE: DNA
<213> ORGANISM: Artificial
<220> FEATURE:
<223> OTHER INFORMATION: Chemically synthesized

<400> SEQUENCE: 22
gccgtccatc ttccttcata                                                    20

<210> SEQ ID NO 23
<211> LENGTH: 20
<212> TYPE: DNA
<213> ORGANISM: Artificial
<220> FEATURE:
<223> OTHER INFORMATION: Chemically synthesized

<400> SEQUENCE: 23
gcacctcgag agaaggacac                                                    20

<210> SEQ ID NO 24
<211> LENGTH: 20
<212> TYPE: DNA
<213> ORGANISM: Artificial
<220> FEATURE:
<223> OTHER INFORMATION: Chemically synthesized

<400> SEQUENCE: 24
ggtcaagtgg agaagggtga                                                    20

<210> SEQ ID NO 25
<211> LENGTH: 20
<212> TYPE: DNA
<213> ORGANISM: Artificial
<220> FEATURE:
<223> OTHER INFORMATION: Chemically synthesized

<400> SEQUENCE: 25
caaagcagct gcaaatacca                                                    20

<210> SEQ ID NO 26
<211> LENGTH: 20
<212> TYPE: DNA
<213> ORGANISM: Artificial
<220> FEATURE:
<223> OTHER INFORMATION: Chemically synthesized

<400> SEQUENCE: 26
ggccaaatgt gtcttccagt                                                    20

<210> SEQ ID NO 27
<211> LENGTH: 20
<212> TYPE: DNA
<213> ORGANISM: Artificial
<220> FEATURE:
<223> OTHER INFORMATION: Chemically synthesized

<400> SEQUENCE: 27
gcaccaagaa atccctgaaa                                                    20

<210> SEQ ID NO 28
<211> LENGTH: 20

```
<212> TYPE: DNA
<213> ORGANISM: Artificial
<220> FEATURE:
<223> OTHER INFORMATION: Chemically synthesized

<400> SEQUENCE: 28
gagggcagtt ggagtagcag                                                 20

<210> SEQ ID NO 29
<211> LENGTH: 20
<212> TYPE: DNA
<213> ORGANISM: Artificial
<220> FEATURE:
<223> OTHER INFORMATION: Chemically synthesized

<400> SEQUENCE: 29
cccctacaag tccaagacca                                                 20

<210> SEQ ID NO 30
<211> LENGTH: 20
<212> TYPE: DNA
<213> ORGANISM: Artificial
<220> FEATURE:
<223> OTHER INFORMATION: Chemically synthesized

<400> SEQUENCE: 30
gagccacaca cccacctaat                                                 20

<210> SEQ ID NO 31
<211> LENGTH: 20
<212> TYPE: DNA
<213> ORGANISM: Artificial
<220> FEATURE:
<223> OTHER INFORMATION: Chemically synthesized

<400> SEQUENCE: 31
atacaggtgc caggaaggtg                                                 20

<210> SEQ ID NO 32
<211> LENGTH: 19
<212> TYPE: DNA
<213> ORGANISM: Artificial
<220> FEATURE:
<223> OTHER INFORMATION: Chemically synthesized

<400> SEQUENCE: 32
gtggatactc gggtggcta                                                  19

<210> SEQ ID NO 33
<211> LENGTH: 20
<212> TYPE: DNA
<213> ORGANISM: Artificial
<220> FEATURE:
<223> OTHER INFORMATION: Chemically synthesized

<400> SEQUENCE: 33
gcctcaaacc ttccaaatca                                                 20

<210> SEQ ID NO 34
<211> LENGTH: 20
<212> TYPE: DNA
```

```
<213> ORGANISM: Artificial
<220> FEATURE:
<223> OTHER INFORMATION: Chemically synthesized

<400> SEQUENCE: 34
gtgaagtcgg ccaaagttgt                                              20
```